United States Patent [19]
Gentile et al.

[11] Patent Number: 5,837,234
[45] Date of Patent: Nov. 17, 1998

[54] BIOARTIFICIAL ORGAN CONTAINING CELLS ENCAPSULATED IN A PERMSELECTIVE POLYETHER SUFLFONE MEMBRANE

[75] Inventors: Frank T. Gentile, Warwick; Shelley R. Winn, Smithfield; Michael Lysaght, East Greenwich, all of R.I.; Ulrich Baurmeister, Germany; Friedbert Wechs; Henning Röttger, both of Wörth, Germany

[73] Assignee: CytoTherapeutics, Inc., Lincoln, R.I.

[21] Appl. No.: 488,317

[22] Filed: Jun. 7, 1995

[51] Int. Cl.$^6$ .............................. C12N 11/04; C12N 5/00; C12N 11/08; A61F 2/00
[52] U.S. Cl. .................. 424/93.7; 424/424; 435/180; 435/182; 435/382; 435/395; 435/401
[58] Field of Search ................................... 535/174, 180, 535/182, 240.22, 240.241, 240.282, 382, 395, 401; 424/93.7, 424

[56] References Cited

U.S. PATENT DOCUMENTS

| | | | |
|---|---|---|---|
| 4,720,343 | 1/1988 | Walch et al. | 210/500.28 |
| 4,892,538 | 1/1990 | Aebischer et al. | 604/891.1 |
| 4,923,608 | 5/1990 | Flottmann et al. | 210/500.25 |
| 4,968,733 | 11/1990 | Müller et al. | 521/64 |
| 4,976,859 | 12/1990 | Wechs | 210/500.23 |
| 5,009,824 | 4/1991 | Walch et al. | 264/45.1 |
| 5,049,276 | 9/1991 | Sasaki | 210/500.23 |
| 5,178,765 | 1/1993 | Hu et al. | 210/651 |
| 5,182,111 | 1/1993 | Aebischer et al. | 424/424 |
| 5,246,582 | 9/1993 | Sluma et al. | 210/500.23 |
| 5,277,811 | 1/1994 | Moya | 210/500.3 |
| 5,284,761 | 2/1994 | Aebischer et al. | 435/182 |

FOREIGN PATENT DOCUMENTS

| | | |
|---|---|---|
| 147 939 | 7/1985 | European Pat. Off. . |
| 576 830 | 1/1994 | European Pat. Off. . |
| WO 91/00119 | 1/1991 | WIPO . |
| WO 91/10425 | 7/1991 | WIPO . |
| WO 92/07525 | 5/1992 | WIPO . |
| WO 92/19195 | 11/1992 | WIPO . |
| WO 93/00439 | 1/1993 | WIPO . |
| WO 93/03901 | 3/1993 | WIPO . |
| WO 93/21902 | 11/1993 | WIPO . |
| WO 94/00222 | 1/1994 | WIPO . |
| WO 94/05406 | 3/1994 | WIPO . |
| WO 94/25503 | 11/1994 | WIPO . |

OTHER PUBLICATIONS

Mark D. Lindner, et al., "Implantation of Encapsulated Catecholamine and GDNF–Producing Cells in Rats with Unilateral Dopamine Depletions and Parkinsonian Symptons," *Experimental Neurology*, 132, 62–76 (1995).

Klomp, F. Gregory, et al., "Macroporous Hydrogel Membranes For A Hybrid Artificial Pancreas. II. Biocompatibility," *Journal of Biomedical Materials Research*, 17, pp. 865–871 (1983).

Lacy, E. Paul, et al., "Maintenance Of Normoglycemia In Diabetic Mice By Subcutaneous Xenografts Of Encapsulated Islets," *Science*, 254, pp. 1782–1784 (1991).

Ronel, H. Samuel, et al., "Macroporous Hydrogel Membranes For A Hybrid Artificial Pancreas. I. Synthesis And Chamber Fabrication," *Journal of Biomedical Materials Research*, 17, pp. 855–864 (1983).

Zondervan, J. G., et al., "Design Of A Polyurethane Membrane For The Encapsulation Of Islets Of Langerhans," *Biomaterials*, 13, pp. 136–144 (1992).

Primary Examiner—David M. Naff
Attorney, Agent, or Firm—Ivor R. Elrifi; Mintz Levin

[57] ABSTRACT

A bioartificial organ for implanting to provide a therapeutic effect is prepared containing a core of living cells encapsulated in a foam-like membrane having three regions: a dense, fine-pored, permselective inner region, a middle region that lacks macrovoids and a fine-pored outer region. The membrane has a molecular weight cutoff that permits passage to nutrients to the cells but not passage of the cells. Preferably, the membrane is made of polyether sulfone, pores range in size between 0.02 μm and 2.0 μm and have polyhedrally symmetric boundaries and are arranged asymmetrically from one surface to the other. The membrane has an asymmetry factor AF relative to the maximum pore diameter of 0.01 to 2.0 and a ratio of the maximum mean free path length to the diameter of the largest pore of greater than 3. The membrane can be hydrophobic or hydrophilic. The bioartificial organ is formed by coextrusion or by stepwise assembly by forming the cell core and then applying the membrane. A polyether sulfone membrane is prepared from a solution containing by weight 12 to 35% polyether sulfone and 15 to 65% ε-caprolactam, and optionally 0 to 85% latent solvent, 0 to 15% thickner, to 5% non-solvent and 0 to 1% auxiliaries. Cells encapsulated can be cells that produce a neurotransmitter such as dopamine or a biologically active factor such as CNTF, NGF, GDNF, endorphins, catecholamines or enkephalins.

18 Claims, 11 Drawing Sheets

BIOARTIFICIAL ORGAN CONTAINING CELLS ENCAPSULATED IN A PERMSELECTIVE POLYETHER SUFLFONE MEMBRANE

FIELD OF THE INVENTION

This invention relates to bioartificial organs for the treatment of diseases or disorders with encapsulated cells that provide neurotransmitters, neuromodulators, hormones, trophic factors, growth factors, or other biologically active molecules. In particular, the bioartificial organs comprising an open-pored foam-like membrane lacking macrovoids.

BACKGROUND OF THE INVENTION

Many diseases or disorders, particularly neurological disorders, appear to be based, in whole or in part, on the absence or limited availability of such biologically active molecules. For example, paralysis agitans, more commonly known as Parkinson's disease, is characterized by a lack of the neurotransmitter dopamine within the striatum of the brain, secondary to the destruction of the dopamine secreting cells of the substantia nigra.

Another example is amyotrophic lateral sclerosis, a disease involving progressive degeneration of motor neurons of the spinal cord, brain stem and cerebral cortex.

For such diseases and disorders, it may be desirable to implant bioartificial organs (BAOs) containing cells within a living host. The living cells secrete a biologically active molecule or provide a needed metabolic function to the recipient. At least a portion of the membrane encapsulating the cells is semipermeable or permselective membrane. This allows the diffusion of nutrients to the cells and the diffusion of wastes and therapeutic molecules out of the device.

It may be desirable to protect the implanted cells from the host's immune system by using an immunoisolatory membrane. This is essential (without immunosuppression) where the implanted cells are xenogeneic to the host. It is also generally required where the cells are allogeneic to the host.

Nutrients must diffuse into the capsule and waste products must be able to leave the capsule to maintain cell viability. In some instances, a necrotic core in the BAO may develop over time due to a shortage of certain metabolites reaching the center of the capsule or the buildup of toxic products. The necrotic core may not contribute to the function of the BAO. Further, the necrotic tissue may also release factors which are detrimental to the surviving cells (e.g., factors which elicit a macrophage or other immune response).

Where immunoisolation is not required, e.g., where the implanted cells are syngeneic or autologous to the host, it is generally desirable to encapsulate the cells with a device having a membrane which prevents the migration of cells out of the device.

It is desirable that implanted BAOs be removeable from the patient if, for example, the therapy has a designated endpoint, such as the administration of growth hormone to an individual. In such cases, the BAO must be sufficiently durable to withstand being removed.

Microencapsulation which typically involves the containment of a single cell or a small number of cells within an essentially spherical membrane. See, e.g., Lim et al., *Science*, 210, pp. 908–910 (1980); Sun, A. M., *Methods in Enzymology*, 137, pp. 575–80 (1988).

Macroencapsulation typically involves loading larger numbers of cells within larger devices that are more readily retrievable than microspheres. See, e.g., Dunleavy et al. (WO 93/03901); Chick et al. (U.S. Pat. No. 5,002,661).

Prior art BAOs have been fabricated from several different types of semipermeable membranes. These BAOs suffer deficiencies associated with the properties of these semipermeable membranes.

For example, in many prior art membranes, much of the internal volume is taken up by macrovoids devoid of polymer. These macrovoids diminish the mechanical strength of the membranes. As a result, BAOs incorporating such membranes tend to be fragile. Care is required during their fabrication, implantation and retrieval to prevent damage. Secondary problems associated with membrane damage include immunological rejection, the possibility of infection by pathogens and potential tumorigenicity.

For example, the membrane used by Zondervan, "Design of a Polyurethane Membrane for the Encapsulation of Islets of Langerhans," *Biomaterials*, 13, pp. 136–44 (1992), is a polyurethane membrane that scanning electron micrographs (SEM) show contains large voids. The HEMA hydrogel membrane disclosed by Ronel and Klomp, "Macroporous Hydrogel Membranes for a Hybrid Artificial Pancreas. I. Synthesis and Chamber Fabrication," *J. Biomed. Materi. Res.*, 17, pp. 855–64 (1983) and Klomp, et al., "Macroporous Hydrogel Membranes for a Hybrid Artificial Pancreas. II. Biocompatibility," *J. Biomed. Materi. Res.*, 17, pp. 865–71 (1983), also have large macrovoids, as evidenced by SEM cross section.

Many prior art BAO membranes that are selectively permeable rely for that property on a thin, essentially two-dimensional permselective surface "skin." This skin can be on the external surface of the membrane, the internal surface, or both. The location of the permselective layer(s) on the membrane surface(s) requires that care be taken not to damage the surface of the BAO during handling and filling of the device. Even localized damage to a permselective skin reduces the permselectivity of a device. For example, Aebischer (U.S. Pat. No. 5,011,472) teaches a cell-containing device having a semipermeable membrane which may be formed from a variety of polymers, having one or more "skins". Faustman, et al (WO 93/03901) refers to an implantable extravascular device having a skinned poly(acrylonitrile-co-vinyl chloride) ("PAN/PVC") membrane with a "critically smooth" exterior surface.

It is desirable to have a permselective membrane wherein the separation zone is not a skin but is below the membrane surface, internal to the membrane.

In addition, many membranes of the prior art contain large proportions of pores with closed cells which play no role in the transport abilities of the membranes and yet weaken the membranes. It is desireable to form a BAO using a membrane having open pores.

Various prior art BAO's foul when contacted with protein-containing fluids, either upon implantation in a living host or during loading of a device. This is due to proteins adsorbing to the membrane surface. This fouling results in deterioration of the transport characteristics of the membrane over time. Typically, the more hydrophobic the membrane, the more easily it fouls.

PTFE, polyethylene and polypropylene are all hydrophobic membranes. Moderately hydrophilic membranes include PAN/PVC and cuprophane.

It is desirable to form a BAO using a hydrophilic membrane material which shows more consistent or unchanged transport properties upon exposure to proteins.

Fabrication of BAOs requires that membranes be sealed with reliable, cell-tight seals that remain intact for the life of the device. Many prior art BAOs are formed from membrane materials that are difficult to seal once the porous surfaces have been exposed to protein-containing cell solutions. In particular, conventional sealing techniques such as heat sealing and crimping have yielded unsatisfactory long-term results for these BAOs. While "dry" seals have been achieved by avoiding membrane contact with protein-containing solutions before sealing, such techniques are difficult, time consuming and add considerably to the manufacturing expense. It is desirable to have a membrane material which could be reliably heat sealed utilizing conventional closure techniques after exposure of the membranes to protein-containing solutions.

Many prior art BAOs comprise hydrophobic membranes that require the addition of a humectant, such as glycerol, to maintain their open, porous structures while stored outside of an aqueous medium. The humectant generally must be removed from the membrane prior to implantation of the device in a subject, requiring additional processing steps in the manufacture of the device. It is desirable to eliminate the necessity to impregnate the membrane with humectant.

For implantation into an individual, BAOs must be sterile. Materials may be sterilized by autoclaving, irradiation or chemical treatment. The generally preferred method is autoclaving because of its ease and safety in handling. An autoclave utilizes superheated steam under pressure to eliminate unwanted biological contaminants. Many membrane materials, which have been used in BAOs cannot tolerate autoclaving. Typically, any polymeric material which decomposes before it melts cannot tolerate autoclaving. Prior art membranes used in bioartifical organs that are not autoclavable include PAN/PVC and polyacrylonitrile. Exposure to hot steam causes damage to the membrane, rendering it unsuitable for use in a BAO. It is desirable to have an autoclavable membrane material for use in a BAO.

BAOs must be biocompatible for the duration of the life of the devices, which can be months or years. Some BAOs have been fabricated from membranes with inadequate long-term biocompatibility. For example, Mandel (WO 91/00119) teaches the use of thin walled, large pore hydrophobic membranes made of polyethylene, polypropylene, polyacrylonitrile or Goretex™, which induce vascularization about the membrane upon implantation. It is desireable to have a BAO formed from a membrane that exhibits satisfactory long term viability.

SUMMARY OF THE INVENTION

The present invention addresses the foregoing problems by providing a bioartificial organ that comprises an open pore foam-like membrane lacking macrovoids. These BAOs are biocompatible, resist fouling, and can be heat sterilized and heat sealed using conventional techniques. These BAOs do not require use of a humectant during storage. BAOs fabricated from such membranes have greater mechanical strength (ranging between 100–150 gms tension), and are thus more easily retreived.

Because the permselective region of these membranes are thicker than a permselective skin and provides a permselective separation zone below the surface of the BAO, the BAOs are more tolerant of surface damage. The invention also provides methods for making these bioartificial organs, and for treating patients with these BAOs.

BRIEF DESCRIPTION OF THE DRAWINGS

FIG. 1A shows a Type 1 macrovoid-containing membrane, FIG.1B shows a Type 2 macrovoid-containing membrane, FIG. 1C–E shows a Type 4 macrovoid-containing membrane.

DEFINITIONS

Figure 1A:
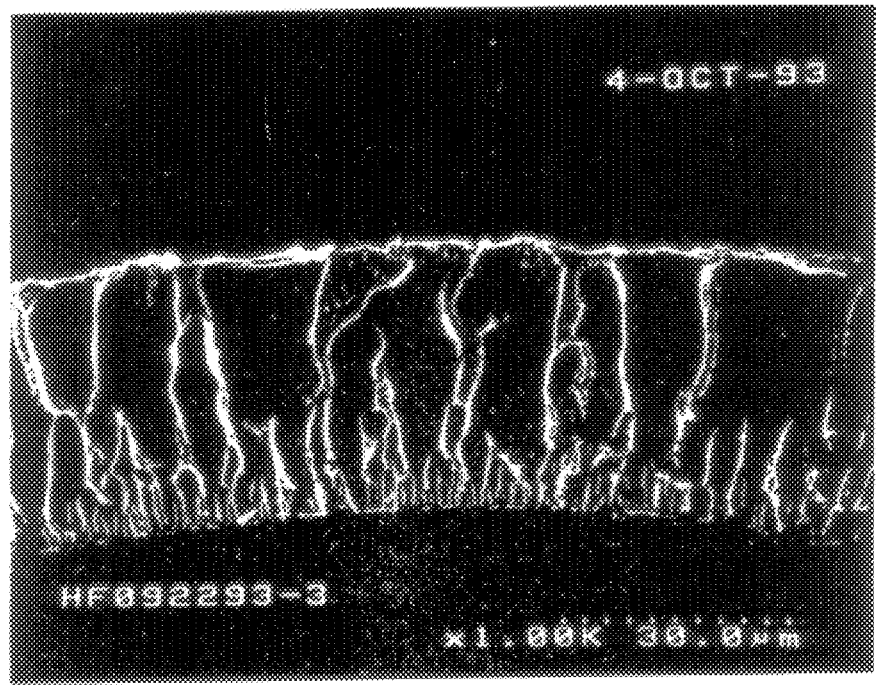
FIG. 1A–1C are scanning electron micrographs of a cross-section of a PAN/PVC membrane used in prior art BAOs, showing macrovoid structure and a skinned Ipermselective surface.
Figure 1B:
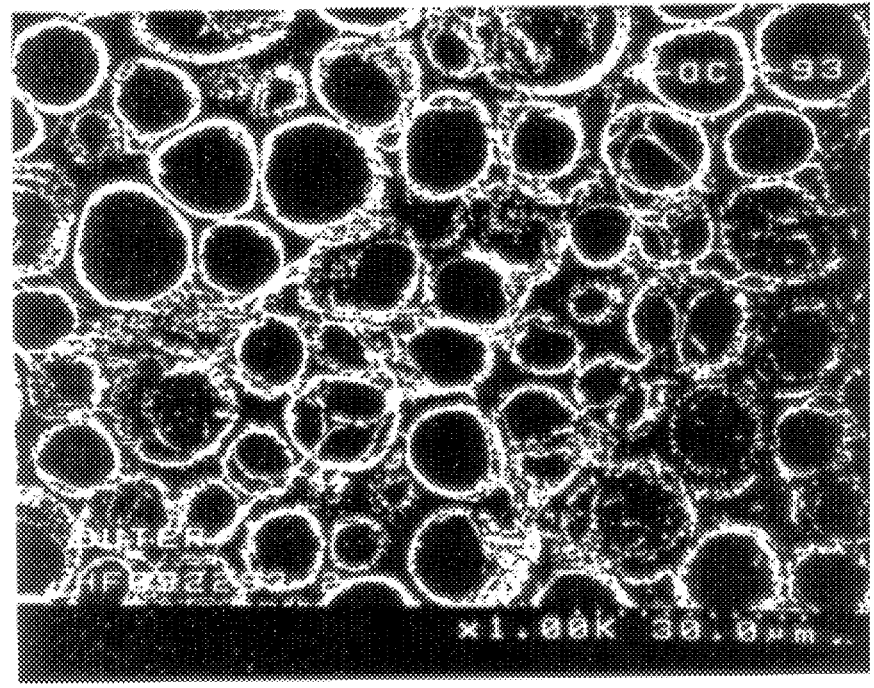
Figure 1C:
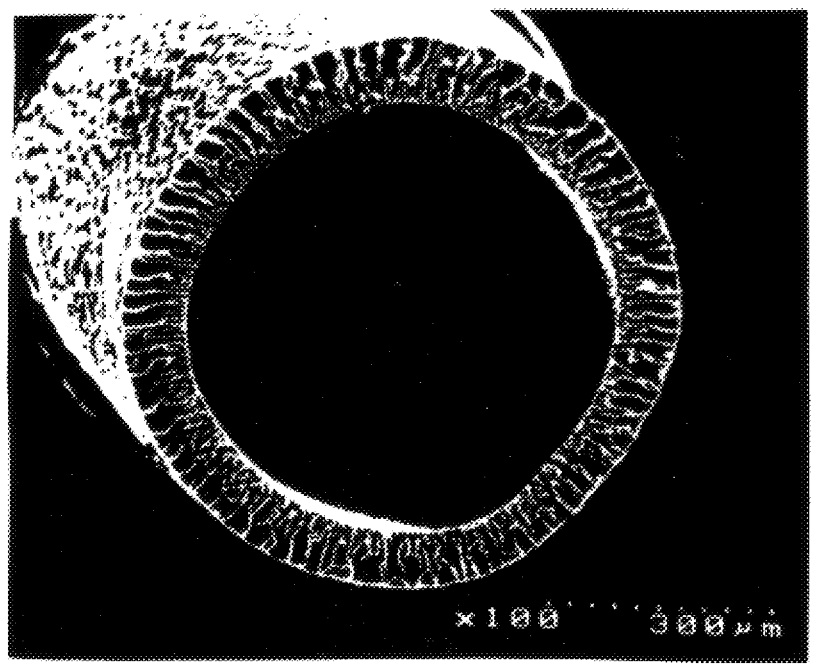
Figure 1D:
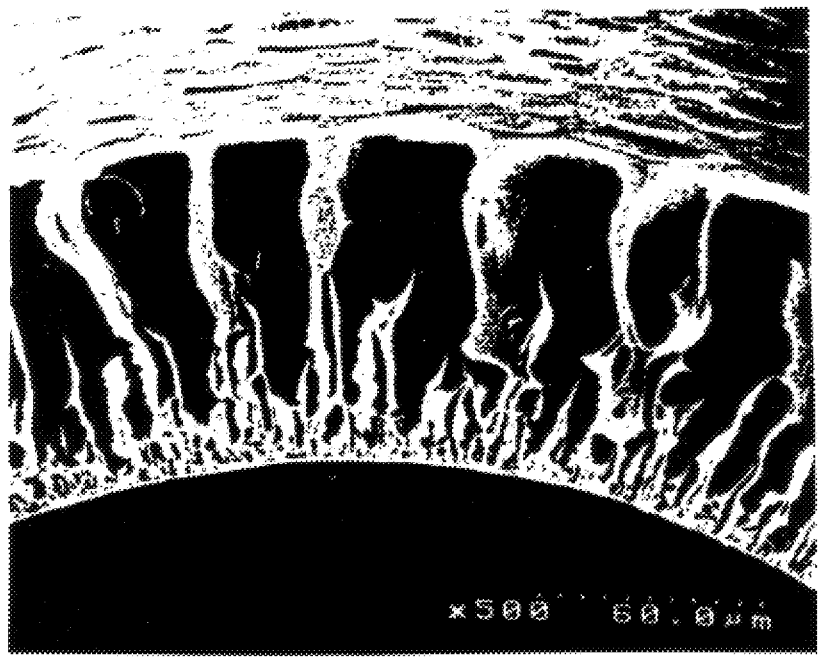
Figure 1E:
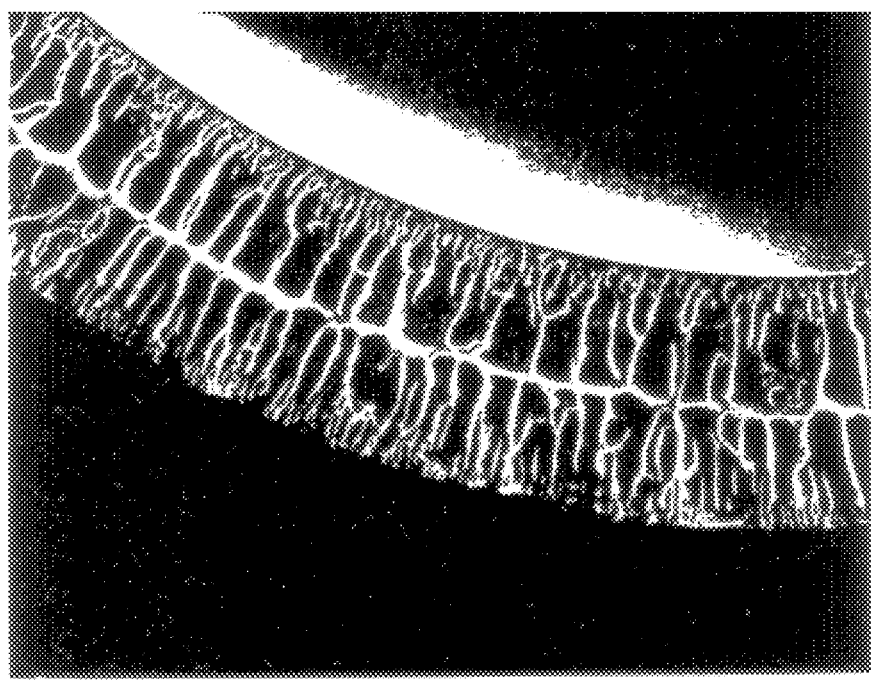
Figure 2A:
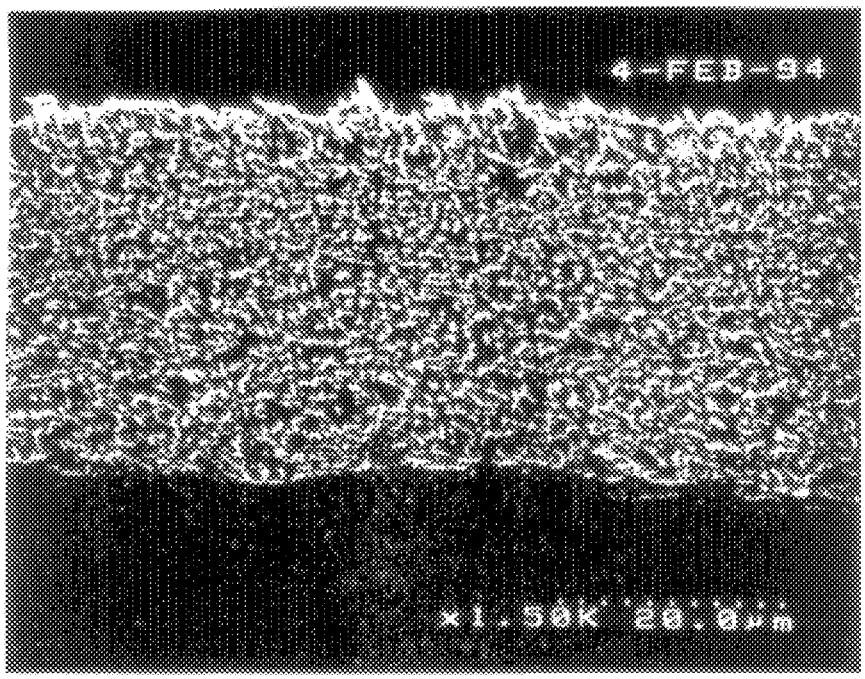
FIG. 2 is a scanning electron micrograph of a cross-section of an open pore polyether sulfone membrane lacking macrovoids used in one embodiment of the BAOs of this invention.
Figure 2B:
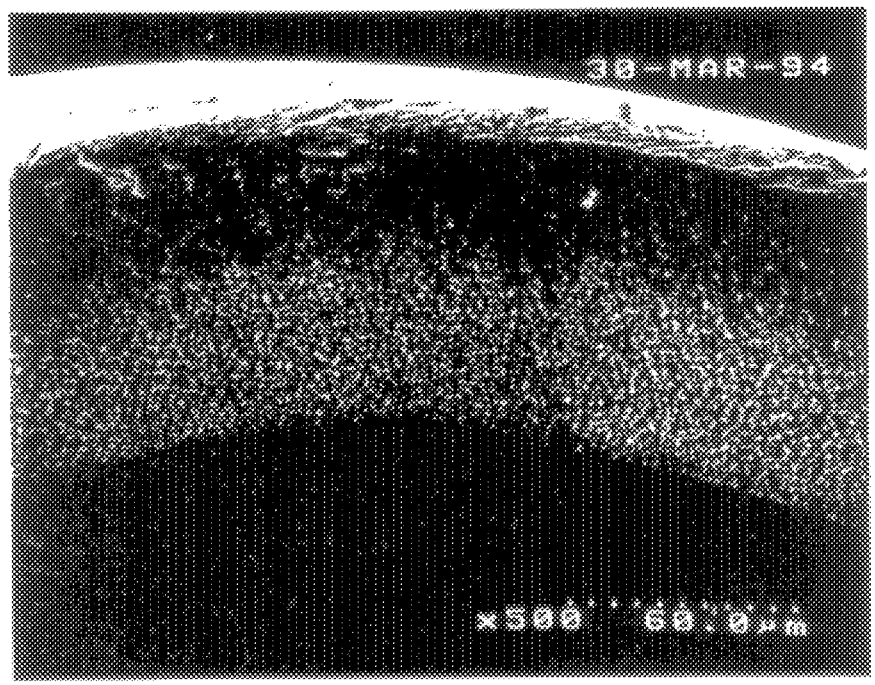

As used herein, a "bioartificial organ" or "BAO" is a device which may be designed for implantation into a host or which may be made to function extracorporeally and either be permanently or removably attached to a host. A BAO contains cells or living tissues which produce a biologically active molecule that has a therapeutic effect on the host. The BAO, upon implantation in a host recipient, should be biocompatible. Accordingly, the BAO should not elicit a detrimental host response sufficient to render it inoperable or not therapeutically useful. Such inoperability may occur, for example, by formation of a fibrotic structure around the device limiting diffusion of nutrients to the cells therein. Detrimental effects may also include rejection of the device or release of toxic or pyrogenic compounds (e.g. synthetic polymer by-products) from the BAO to surrounding host tissue. BAOs may have numerous capsule configurations, such as cylindrical, disk-shaped or spherical. The BAO is useful (a) to deliver a wide range of cellular products, including high molecular weight products, to an individual in need of them, and/or (b) to provide needed metabolic functions to an individual, such as the removal of harmful substances.

BAOs comprising encapsulated cells may be constructed with immunoisolatory properties which hinder elements of the host immune system from entering the organ, thereby protecting the cells contained within the bioartificial organ from detrimental immune destruction. Immunoisolatory properties, however, may not be necessary in all cases (e.g., if the cells are autologous or syngeneic to the host). The use of a BAO increases the diversity of cell types that can be employed in therapy.

A "biologically active molecule" is one which (a) may function within the cell in which it is made or (b) may be expressed on the cell surface and affect the cell's interactions with other cells or biologically active molecules (e.g., a neurotransmitter receptor or cell adhesion molecule), or (c) may be released or secreted from the cell in which it is made and exert its effect on a separate target cell or target molecule in the host (e.g., a neurotransmitter, hormone, growth factor, or cytokine).

As used herein, unless otherwise specified, the term "cells" means cells in any form, including but not limited to cells retained in tissue, cell clusters, and individually isolated cells. The cells used in this invention produce at least one biologically active molecule.

Furthermore, the "core" of cells used herein include both cells, as defined above, and any other materials or medium which support or promote the function of the cells. Specifically, materials can be used to suspend the cells, to distribute the cells, to anchor the cells or to sustain the cells. For example, extracellular matrix (ECM) components can be included to promote specific attachment or adhesion of the isolated cells. One example of such material is described in U.S. Pat. No. 5,182,111 wherein two types of cells are encapsulated in one bioartificial organ and one type of cells secrete factors which augment the secretion of biologically active factors from the second type of cells. Another example of materials which could be included in the core containing cells are molecules and factors which control growth and differentiation of cells. These are more completely described in co-pending U.S. application Ser. No. 08/279,773, filed Jul. 20, 1994 and 08/432,698, filed May. 9, 1995.

DETAILED DESCRIPTION OF THE INVENTION

This invention is directed to an improved BAO comprising a foam-like membrane having 3 regions: a dense, fine-pored, permselective inner region next to the lumen, a middle region that lacks macrovoids, and a fine-pored outer region. Across the entire thickness of the membrane is a system of fine pores forming a network structure that is open.

The transport properties of these membranes are determined by the dense inner region. Rather than a separation "skin" of prior art membranes, the separation occurs over a region of dense fine pores in this membrane. This dense fine-pored region is thicker than the previous, essentially two-dimensional "skin" structures and extends below the inner surface of the membranes.

Suitable membranes having a fine-pored foam-like structure lacking macrovoids are described, e.g., in Wechs (U.S. Pat. No. 4,976,859) and Muller (U.S. Pat. No. 4,968,733) both of which are hereby incorporated by reference. Although these membranes have been used in microfiltration or ultrafiltration applications, these membranes have not previously been used in the fabrication of BAOs.

Wechs and Muller describe integral membranes wherein the pore system is open pored or open celled throughout. In Wechs, the membranes have a maximum pore diameter ranging between 0.02 µm to 2 µm, measured by the blow point method. The pores typically have polyhedrally symmmetrical boundaries. The ratio of the maximum mean free path length to the diameter of the largest pore is greater than 3, preferably between 5 and 100. The average pore size of membranes according to Wechs changes steadily from one surface to the other surface with asymmetry factor AF relative to the maximum pore diameter preferably being 0.01 to 2. As a result of this asymmetry of the pore system, high permeabilities are achieved. Wechs describes calculation of blow point and AF. In one embodiment of both Wechs and Muller the hollow fiber membrane has, in its outer region, a fine-pored, outwardly open-cell structure which merges into an increasingly coarse-pored texture towards the middle of the membrane. Towards the lumen side, the cells become more compact again and form an open-pored inner surface.

Wechs and Muller also describe methods of making these membranes. For example, Wechs discloses a polyether sulfone membrane created by dissolving 12 to 35% by weight, relative to a total solution, of polyether sulfone in a mixture of 15 to 65% by weight of $\epsilon$-caprolactam, 0 to 85% by weight of latent solvent, 0 to 15% by weight of thickener and 0 to 5% by weight of non-solvent, and a 0 to 1% by weight of auxiliaries.

In Muller, the membrane is formed by a process using a solution comprising of $\epsilon$-caprolactam and at least one of: polyvinylidine fluoride, polyphenylene sulfide, polysulfone, polyacrylonitrile, ethylene/vinyl alcohol copolymer, ethylene/chlorotrifluoroethylene copolymer, polyethersulfone, polyether-imide, polymethyl methacrylate, polycarbonate, cellulose triacetate and copolymers thereof.

Other polymers that may be useful in this invention include polysulfones, co-polymer solutions with PES such as PAN-PES, or any other solutions that could combine with PEG or PVP solvents. We prefer polyether sulfone.

These membranes can be made either hydrophobic or hydrophilic. Hydrophilic membranes such as polyether sulfone membranes, are resistant to fouling. Polyether sulfone membranes show a smaller change in transport properties than PAN/PVC membranes of the prior art, upon exposure to protein-containing solutions.

We prefer hydrophilic membranes for forming the BAOs of this invention. Hydrophilic membranes are also heat-sealable by conventional methods because they are not fouled upon exposure to protein-containing solutions. Thus use of a humectant is unnecessary.

The BAOs of this invention have been able to support the viability of dividing xenogeneic cells in a cerebrospinal fluid implantation site. Dividing cells generally have higher metabolic requirements than non-dividing cells.

Studies with dividing, genetically modified BNK cells encapsulated in prior art double-skinned PAN/PVC membranes showed only limited cell viability after 30 days in the sheep intrathecal space. The BAOs of this invention using the same cells encapsulated in polyether sulfone membranes permitted significantly greater cell viability (measured by abundance and health of the cells in the same animal model).

The BAOs of this invention may have a wide range of MWCOs by simple changes in the manufacturing conditions used to form the membranes. It is possible to form membranes having a wide variety of MWCOs using a single polymer formulation, and varying only the composition of the lumen forming solution (or the coagulant bath solution). See, infra. Thus, the toxicity of various membranes made from a single formulation need not be retested.

In general, the molecular weight cutoff of the membrane may be varied by the water content of the lumen forming solution or bore solution. The higher the water content, the smaller the pore size. Alternately, such manipulation of the MWCO may be accomplished by varying the water content of the coagulant bath solution.

As a result of having the MWCO of the membrane in the interior of the membrane rather than on the outside skin, it is also easier to keep the MWCO constant during manufacture of the membrane. With prior membranes, the morphology of the outer skin is fixed by a quench bath. However the chemical composition of the quench bath is difficult to keep constant due to the membrane chemicals that leach out into the quench bath and degrade the bath over time.

The permselective nature of the membrane allows passage of substances up to a predetermined size, but prevents the passage of larger substances. The molecular weight cutoff (MWCO) selected for a particular vehicle will be determined in part by the type and extent of immunological rejection it is anticipated will be encountered after the BAO is implanted and in part by the molecular size of the largest substance to be allowed to pass into and/or out of the BAO.

The type and extent of immunological attacks which may be mounted by the recipient following implantation of the BAO depend in part upon the encapsulated material and in part upon the identity of the recipient (i.e., how closely the recipient is genetically related to the source of the cells).

When the implanted tissue is allogeneic to the recipient, immunological rejection may proceed largely through cell-mediated attack by the recipient's immune cells against the implanted cells. When the tissue is xenogeneic to the recipient, molecular attack through assembly of the recipient's cytolytic complement attack complex may predominate, as well as the antibody interaction with complement.

The MWCO of the surrounding region must therefore be sufficiently low to prevent access of substances required to carry out these attacks to the core, yet sufficiently high to allow delivery of the needed product to the recipient's body.

The MWCO need not be strictly restricted to a range which excludes immunoglobulin G from the core. In fact, there are many cases in which higher MWCOs are not only permissible but also advantageous. Higher MWCOs allow the delivery of a wide variety of useful products from immunoisolated cells, as well as the use of such cells to provide metabolic control of high molecular weight substances.

Thus, in appropriate cases, the permselective membranes can allow the passage of molecules up to about the size of Clq (about 400 kD), the largest protein required for the assembly of the complement attack complex. Therefore, any cellular product or metabolite below about the size of Clq can pass freely through the BAO.

In other cases, it may still be desirable to exclude immunoglobulins. In such cases, materials which form matrices or membranes through which molecules which are equivalent to or larger than the size of immunoglobulin G (about 150 kD) cannot pass can be used. Cellular products or metabolites which are smaller than about 150 kD will still pass through the vehicle.

In still other cases, where the patient is immunosuppressed or where the implanted tissue is syngeneic to the patient, a vigorous immunological attack is not likely to be encountered, and passage of a high molecular weight molecule may be desired. In these latter cases, materials which allow passage of all molecules up to about the size of immunoglobulin M (about 1,000 kD) can be used. These materials will impede the passage of only very large substances, such as cells.

Microporous membranes generally have a pore size of $0.1\mu$ to $1.0\mu$ and are useful for separating out cells and bacteria. Ultrafiltration membranes generally have a pore size of $0.03\mu$ to $0.1\mu$ and a corresponding MWCO of 5000 to 300,000. Ultrafiltration membranes can be immunoisolatory. Nominal MWCO is typically represented by 90% rejection.

In the BAOs of this invention, the membranes are typically characterized by having a hydraulic permeability ranging between 4–650 $ml/min/m^2/mmHg$.

Biocompatibility of the membrane is produced by a combination of factors. First, the materials used to form the BAO are substances selected based upon their ability to be compatible with, and accepted by, the tissues of the recipient of the BAO. Second, substances used in preparing the BAO should be either free of leachable pyrogenic or otherwise harmful, irritating, or immunogenic substances or should be exhaustively purified to remove such harmful substances.

The membrane can optionally include substances which decrease or deter local inflammatory response to the implanted vehicle, and/or generate or foster a suitable local environment for the implanted cells or tissues. For example, antibodies to one or more mediators of the immune response could be included. Available potentially useful antibodies such as antibodies to the lymphokines tumor necrosis factor (TNF), and interferon (IFN) can be included in the matrix precursor solution. Similarly, an anti-inflammatory steroid can be included. Christenson, L., et al., *J. Biomed. Mat. Res.*, 23, pp. 705–718 (1989); Christenson, L., Ph.D. thesis, Brown University (1989), both herein incorporated by reference. Alternatively, a substance which stimulates angiogenesis (ingrowth of capillary beds) can be included; this may be particularly desirable where the isolated cells or tissues require close contact with the recipient's bloodstream to function properly (e.g., insulin-producing islets of Langerhans). Cells which are genetically engineered to secrete antibodies may also be included in the matrix.

Making a BAO from the Membrane

The BAOs of this invention may be fabricated as follows. In one embodiment, the BAO is formed by a coextrusion technique, according to the methods of issued U.S. Pat. Nos. 5,284,761, 5,232,712, or 5,182,111, herein incorporated by reference, wherein a cell suspension and a polymeric solution are extruded through a common extrusion port having concentric pores. Preferably, the polymeric solution used in this method is the solution described in U.S. Pat. Nos. 4,976,859, or 4,968,733.

In another embodiment of the present method, the BAO is formed by stepwise assembly. We prefer stepwise assembly. For example, the cell core could be formed initially, and then the encapsulating membrane applied or assembled. The membrane can either be formed by extrusion or by molding.

A patch- or sheet-shaped membrane may be formed by stepwise extrusion of calendered sheets. In this embodiment, a sheet of core material is layered onto a sheet of "fine pored" membrane material, then covered by a second sheet of "fine pored" membrane material. The edges of the BAO are then sealed by crimping, compressing, heating, sealing with a biocompatible glue, or binding to a preformed biocompatible impermeable clip or combinations of the above.

Conversely, the encapsulating membrane can be preformed, and then filled with the preformed core of cells (for instance, using a syringe). Then the BAO is then sealed.

Alternatively, a patch- or sheet-shaped matrix core can be formed by molding, then sandwiched between sheets of "fine pored" membrane and sealed or clipped in the manner described above to complete the isolation of the core materials.

Although any suitable method of sealing the BAO may be used, such as the employment of polymer adhesives and/or crimping, knotting and heat sealing, all of which are known in the art, heat sealing is most preferred because it is less time consuming and less expensive.

Although less preferable, any suitable "dry" sealing method can also be used. In such methods, a substantially non-porous fitting is provided through which the cell-containing solution is introduced. Subsequent to filling, the BAO is sealed. Such a method is described in copending U.S. application Ser. No. 08/082,407, filed Jun. 23, 1993, now abandoned, herein incorporated by reference.

Preferably, the device also includes a matrix to enhance cell distribution and viability, as described in Dionne et al., WO 92/19195.

The device also preferably includes a tether for ease in retrieval, as described in Dionne et al., WO 92/19195.

Cells Encapsulated By the BAO

The choice of cells in a BAO depends upon the intended application. A wide variety of cells may be used in this invention. These include well known, publicly available immortalized cell lines as well as dividing primary cell cultures. Examples of publicly available cell lines suitable for the practice of this invention include, L-6 cells, MDCK cells, LLC-PK cells, β-CH3 cells, C2 cells, baby hamster kidney (BHK), Chinese hamster ovary (CHO), mouse fibroblast (L-M), NIH Swiss mouse embryo (NIH/3T3), African green monkey cell lines (including COS-a, COS-1, COS-6, COS-7, BSC-1, BSC-40, BMT-10 and Vero), rat adrenal pheochromocytoma (PC12), rat glial tumor cells (C6), RAJI (human lymphoma) cells, MOPC-31C mouse plasmacytoma cells, MN9D cells, MN9H cells, ripTAg transgenic mouse derived cells, SCT-1, β-TC cells, Hep-G2 cells, AT-T20 cells, beta-cell lines such as NIT cells or RIN cells, Ntera-2 cells (Pleasure et al., *Journ. Neuroscience*, 12, pp. 1802–15 (1992)) and human astrocyte cell lines such as U-373 and U-937. We prefer BHK cells.

Primary cells that may be used include, bFGF-responsive neural stem/progenitor cells derived from the CNS of mammals (Richards et al., *PNAS* 89, pp. 8591–8595 (1992); Ray et al., *PNAS* 90, pp. 3602–3606 (1993)), primary fibroblasts, Schwann cells (WO 92/03536), astrocytes, oligodendrocytes and their precursors, myoblasts, and adrenal chromaffin cells.

Myoblasts are one type of cell that may be encapsulated in a BAO according to this invention. Myoblasts are muscle precursor cells originally derived from mesodermal stem cell populations. A number of myoblast cell lines are available which can undergo differentiation in culture, e.g., L-6 and β-CH3 cells. Primary myoblasts can be readily isolated from tissue taken from an autopsy or a biopsy, and can be purified and expanded. Myoblasts proliferate and fuse together to form differentiated, multi-nucleated myotubes. Myotubes no longer divide, but continue to produce muscle proteins. While proliferating, myoblasts may readily be genetically engineered to produce therapeutic molecules. Methods are known for introducing one or more genes into myoblasts to produce the desired biologically active molecules. Myoblasts are capable of migrating, fusing into pre-existing fibers, and serving as carriers for the introduced gene(s). Verma et al. (WO 94/01129); Blau, et al., *TIG*, 9, pp. 269–74 (1993); WO 93/03768; WO 90/15863. The engineered cells may then be encapsulated and allowed to differentiate in the BAO.

The choice of cells also depends upon the intended application. The cells within the BAO may be chosen for secretion of a neurotransmitter. Such neurotransmitters include dopamine, gamma aminobutyric acid (GABA), serotonin, acetylcholine, noradrenaline, epinephrine, glutamic acid, and other peptide neuro-transmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

The cells within the BAO may be chosen for secretion of a neurotransmitter. Neurotransmitter are typically small molecules (less than 100 daltons molecular weight) which act as chemical means of communication between neurons. Such neurotransmitters include dopamine, gamma aminobutyric acid (GABA), serotonin, acetylcholine, noradrenaline, epinephrine, glutamic acid, and other peptide neurotransmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor. Co-pending U.S. application Ser. No. 08/279,773 describes a variety of compounds that can control the growth of cells in a bioartificial organ.

The cells can be chosen for their secretion of biologically active factors such as: hormones, cytokines, growth factors, trophic factors, angiogenesis factors, antibodies, blood coagulation factors, lymphokines, enzymes, and other therapeutic agents or agonists, precursors, active analogs, or active fragments thereof. These include enkephalins, catecholamines, endorphins, dynorphin, insulin, factor VIII, erythropoietin, Substance P, neurotensin, nerve growth factor (NGF), Glial cell line-derived Neurotrophic Factor (GDNF), platelet-derived growth factor (PDGF), epidermal growth factor (EGF), brain-derived neurotrophic factor (BDNF), neurotrophin-3 (NT-3), neurotrophin-4/5, CDF/LIF, bFGF, aFGF, an array of other fibroblast growth factors, ciliary neurotrophic factor (CNTF), and interleukins. In one embodiment we prefer enkephalins, catecholamines, and endorphins.

Any suitable cell may be transfected with a gene encoding a desired biologically acitve molecule. The gene encoding the desired molecule can be obtained using standard cloning techniques. Numerous genes encoding biologically active molecules are known. See, e.g., U.S. Pat. Nos. 5,049,493, 5,082,670 and 5,167,762, all of which are incorporated herein by reference.

The DNA and amino acid sequence of CNTF is known. See U.S. Pat. No. 4,997,929, incorporated herein by reference. The DNA sequence encoding hNGF is known. See Hoyle, *Neuron*, 10, pp. 1019–34 (1993). The DNA sequence encoding GDNF is also known. See Lin, WO 93/06116. In another embodiment, we prefer NGF, GDNF and CNTF, most preferably CNTF.

Cells may also be chosen for their ability to restore or augment vital metabolic functions, such as the removal of toxins or harmful metabolites (e.g., cholesterol) from the bloodstream by cells such as hepatocytes.

Techniques and procedures for isolating cells or tissues which produce a selected product are known to those skilled in the art, or can be adapted from known procedures with no more than routine experimentation.

Four factors are important in determining the number of cells or the amount of tissue to be placed within the core of the BAO. They are more fully discussed in Dionne, WO 92/19195. Briefly, the four factors are: (1) BAO size and geometry; (2) mitotic activity within the BAO; (3) viscosity requirements for core preparation and/or loading; and (4) pre-implantation assay and qualification requirements.

A primary consideration in selecting a particular configuration for the BAO is the access of oxygen and nutrients to the isolated cells or tissues, and passage of waste metabolites, toxins and the secreted product from the BAO. The BAO can be any configuration appropriate for maintaining biological activity and providing access for delivery of the product or function, including for example, cylindrical, rectangular, disk-shaped, patch-shaped, ovoid, stellate, or spherical. Moreover, the vehicle can be coiled or wrapped into a mesh-like or nested structure. If the BAO is to be retrieved after it is implanted, configurations which tend to lead to migration of the BAO from the site of implantation, such as spherical vehicles small enough to travel in the recipient's blood vessels, are not preferred. Certain shapes, such as rectangles, patches, disks, cylinders, and flat sheets offer greater structural integrity and are preferable where retrieval is desired.

Prior to Implantation

The newly-formed BAO can be maintained under sterile conditions in a non-pyrogenic, serum-free defined nutrient medium or balanced salt solution, at about 37° C., prior to implantation. Lower temperatures (20° C.–37° C.) may be optimal for certain cell types and/or culturing conditions. Other holding temperatures and medium compositions consistent with good cell viability may also be used. Alternatively, the BAO can be cryopreserved in liquid nitrogen, if a cryoprotective agent such as glycerin has been incorporated into the matrix. Rajotte, R. V. et al., *Transplantation Proceedings*, 21, pp. 2638–2640 (1989). In such a case, the BAO is thawed before use and equilibrated under sterile conditions as described above.

One or more in vitro assays are preferably used to establish functionality of the BAO prior to implantation in vivo. Assays or diagnostic tests well known in the art can be used for these purposes. See, e.g., *Methods in Enzymology*, Abelson, ed., Academic Press, 1993. For example, an ELISA (enzyme-linked immunosorbent assay), chromatographic or enzymatic assay, or bioassay specific for the secreted product can be used. If desired, secretory function of an implant can be monitored over time by collecting appropriate samples (e.g., serum) from the recipient and assaying them. If the recipient is a primate, microdialysis may be used.

Implantation

The number of BAOs and BAO size sufficient to produce a therapeutic effect upon implantation is determined by the amount of biological activity required for the particular application. In the case of secretory cells releasing therapeutic substances, standard dosage considerations and criteria known to the art are used to determine the amount of secretory substance required. Factors to be considered are discussed in Dionne, WO 92/19195, herein incorporated by reference.

Implantation of the BAO is performed under sterile conditions. Generally, the BAO is implanted at a site in the host which will allow appropriate delivery of the secreted product or function to the host and of nutrients to the encapsulated cells or tissue, and will also allow access to the BAO for retrieval and/or replacement. The preferred host is a primate, most preferably a human.

A number of different implantation sites are contemplated. These implantation sites include the central nervous system, including the brain, spinal cord, and aqueous and vitreous humors of the eye. Preferred sites in the brain include the striatum, the cerebral cortex, subthalamic nuclei and nucleus Basalis of Meynert. Other preferred sites are the cerebrospinal fluid, most preferably the subarachnoid space and the lateral ventricles. This invention also contemplates implantation into the kidney subcapsular site, and intraperitoneal and subcutaneous sites, or any other therapeutically beneficial site.

Specifically, the method of this invention can be used to deliver ciliary neurotrophic factor (CNTF) to a patient suffering from amyotrophic lateral sclerosis (ALS). CNTF may be administered to a patient suffering from ALS using encapsulated CNTF secreting cells. Preferably, the encapsulated cells are placed in the intrathecal subarachnoid space. Intrathecal delivery of the protein will allow it to act directly on the cell body receptor of lower motor neurons (spinal motor neurons) as well as on the upper motor neurons (cortical motor neurons or Betz cells). The latter are inaccessible by systemic delivery, since the blood brain barrier inhibits the diffusion of CNTF directly into the central nervous system (CNS).

CNTF has been shown to support the survival of motor neurons in vitro. CNTF is found predominantly in Schwann cells of peripheral nerves, and promotes the survival of a variety of neuronal and glial cells. CNTF was initially isolated from sciatic nerve (Collins, Franklin D., U.S. Pat. No. 4,997,929), and the protein sequence for rat, rabbit and human CNTF has been determined. The ameliorating effects of CNTF have been shown in several animal models of motor neuron disease, including the Motor Neuron Degeneration (Mnd) mouse, the Wobbler mouse and the Progressive Moter Neuronopathy (Pmn) mouse. Lindsay, Ronald, 15, *Neurobiology of Aging*, pp. 249–251, 1994.

CNTF has been administered systemically in clinical trials in humans; however, the trials have been halted, reportedly due to the appearance of side effects including cough, weight loss, and flu-like symptoms. One of the disadvantages of parenteral administration of the dissolved recombinant protein is the CNTF cannot be delivered continuously, the theoretically best route of administration. It is hypothesized that continuous administration of CNTF may prevent the down regulation of the CNTF receptor typically occurring with repeated bolus injections. Further, the factor is known to have a short half-life (of approximately 200 minutes in the human body) and is very unstable molecule, so administration via infusion pump is likely to be ineffective. Sendtner, 358 *Nature*, August 1992, pp. 502–504, reported transfecting mouse D3 cells with the CNTF sequence and injecting the naked cell intraperitoneally into Pmn mice. While Sendtner reported that mice receiving the CNTF transfected D3 cells showed an improved motor performance than untreated mice, and that the CNTF treatment exhibit a protective effect, the animals receiving the tumor cells injections showed intraperitoneal growth of teratoma-like tissue.

Encapsulation of cells may prevent the formation of tumors created by the introduction of cells from cell lines, such as was shown by Sendtner.

In order that this invention be better understood, the following examples are set forth. These examples are for purposes of illustration only, and are not to be construed as limiting the scope of this invention in any manner.

EXAMPLES

Example 1

Manufacturing of PES membranes

A series of synthetic hydrophilic PES membranes both ultrafiltration and microporous ($\mu$p) were manufactured. Fiber nos. 1–4 has microporous characteristics. Both types of membranes are manufactured according to the following procedure:

Preparation of the spinning solution 17.8 parts of a polyether sulfon (Ultrason 6020 BASF), 1.3 parts of a sulfonated polyether sulfon (degree of sulfonation 7%), 19.1 parts polyvinyl pyrrolidone, 14.3 parts caprolactame, 43.8 parts butyrolactone, 3.8 parts glycerole and 0.6 parts demineralized water were mixed at room temperature by intensive stirring. The obtained slurry was heated up to 115° C. in order to obtain a homogeneous solution. The solution was then cooled to 50° C., degassed and filtered.

Preparation of the hollow fiber membranes

Using a usual hollow fiber nozzle with a circular slit and a needle to introduce the lumen filling liquid, hollow fibers were made from the spinning solution. The temperature of the spinning solution was 30° C.; the temperature of the lumen forming liquid was 25° C. As the spining bath, demineralized water was used. The length of the air gap between the surface of the spinning bath and the nozzle was 60 cm. The obtained fibers were washed with 80° C. water and dryed.

Figure 3:
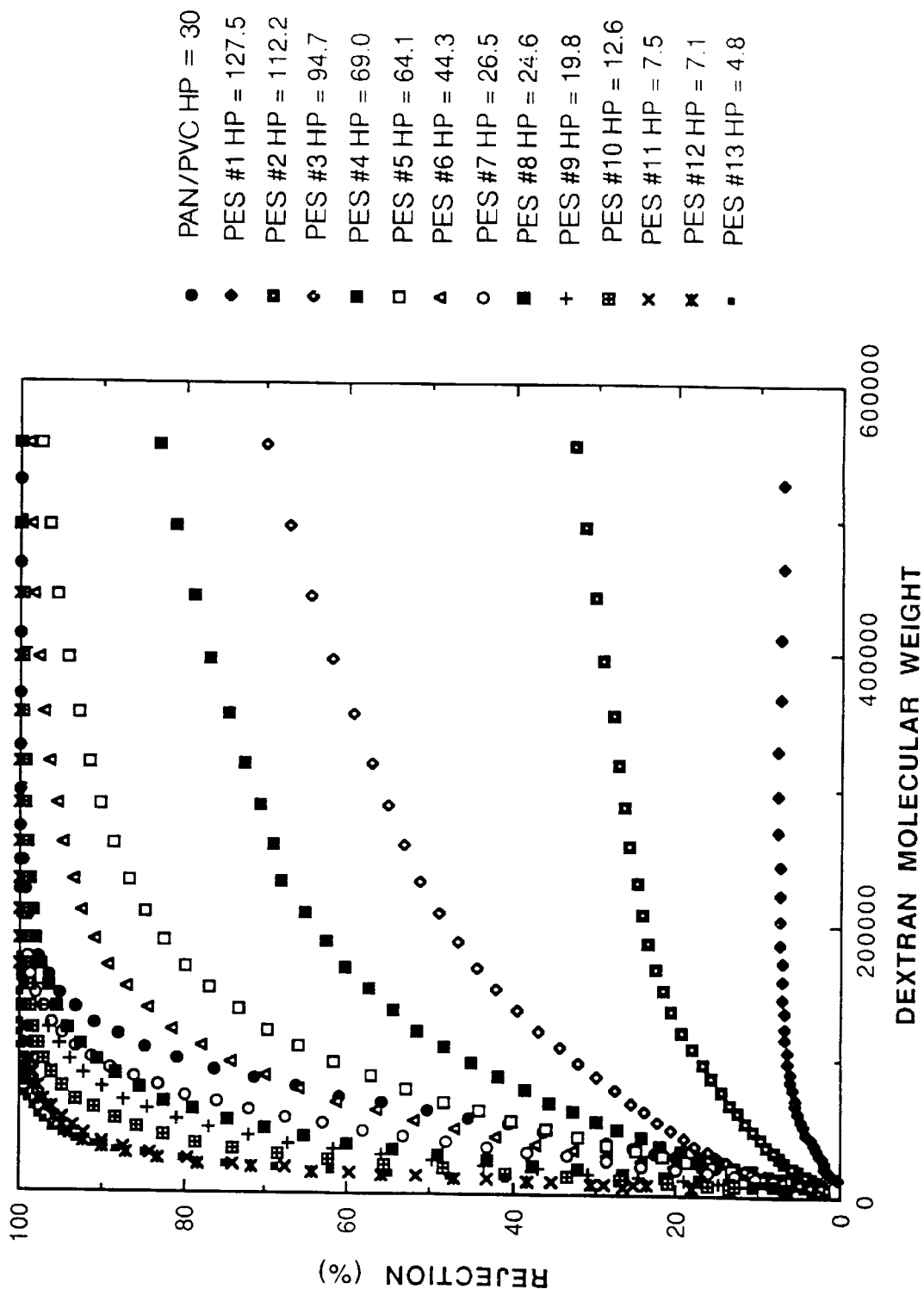
FIG. 3 is a graph showing the retention capacity of dextran molecules by PES membranes nos. 1–13 and a PAN/PVC membrane.

The MWCO of fibers nos. 1–13 are shown in FIG. 3. Several of these fibers were further characterized. The composition of the lumen forming liquid and the hydraulic permeability of the resulting membrane is given in Table 1.

TABLE 1

| Fiber No. | Composition of Lumen (Forming Liquid) in parts | | | Permeability (ml/min·m²·mmHg) |
|---|---|---|---|---|
| | E-Caprolactam | Glycerol | Water | |
| 11 | 43 | 43 | 14 | 7.7 |
| 7 | 44.75 | 44.75 | 10.5 | 25 |
| 5 | 45.25 | 45.25 | 9.5 | 64 |
| 3 | 45.75 | 45.75 | 8.5 | 93 |

As Table 1 and FIG. 3 show, the greater the water content in the lumen forming or bore solution, the lower the MWCO and the hydraulic permeability.high Example 2

Characterization of PES membranes

Synthetic hydrophilic PES membranes for use in the BAOs of this invention may be made according to the method of Example 1 and can be characterized for hydraulic permeability (HP) and convective Molecular Weight Cut-Off (MWCO) according to the following procedures:

Hydraulic Permeability Characterization:

First, the lumen volumetric flow rate is calculated from the equation:

$$Q_L = (nd^3 \gamma_w)/1.64 \times 10^{11} \quad (1)$$

where:
$Q_L$ = average flow through the fiber lumens in ml/min
n = number of fibers in the cartridge.
$\gamma_w$ = wall shear rate, set at 2000 sec$^{-1}$
d = inner diameter of fiber in microns
* Select 15 fibers per cartridge.

Next, the fibers are potted. A bundle of 15 glycerinized and dried fibers should be tied at one end with a small piece of string. Thread the string through the cartridge (Qosina #27222) and place the end of the membrane bundle into the lumen of the test cartridge. Pull the membrane through the device until the bundle is protruding from both ends. Remove the string from the bundle. The test device is ready to be potted with 5 min. epoxy (Cole-Parmer #G-08773-30) one end at a time.

Mix the 5 min. epoxy hardener (Cole-Parmer #G-08773-30) one to one in a small weigh boat with the wooden end of a cotton tip applicator. Carefully apply the epoxy to each end of the device with the applicator. Make sure that the epoxy completely encompasses each fiber extending out from the end of the device to prevent leaks. It is important that the epoxy is applied between each fiber, but does not enter into the lumens of any of the fibers of wick too far into the device.

Hold the device horizontally in the fingertips and gently rotate the device until curing is complete. Rotating helps avoid dripping and extensive wicking of the epoxy as it cures.

Cut to the end of the device exposing the ends of the fibers with a razor once the epoxy is completely cured (after 10 minutes). If the epoxy seeps into the cartridge and does not fill flush to the end so the cartridge, cut the cartridge so that the epoxy is flush to the end of the cartridge. This prevents bubbles from catching at either end of the cartridge during HP and MWCO testing.

Clean the ends of the device of excess epoxy. Measure the length of the exposed fiber between the epoxy cured ends. Use the shortest distance if there is uneven wicking of the epoxy. This is the length used to calculate the hydraulic permeability and the testing time for MWCO testing.

Next, the fibers should be air leaked.

After the cartridge is potted and air leaked, it is placed on a test stand. Attach the cartridge to the test stand by inserting the barbed ends into the silicon tubing (Cole-Parmer #07616-22). The filtration port should be facing down. Disconnect tubing from the inlet of the in-line filter. This in-line filter should only be used for water. Place the Inlet tubing into the water and turn on the pumps. Outlet line goes to waste container. Once the water comes through the other end of the tubing, reattach to the in-line filter.

To set lumen flow and trans membrane pressure, bring the lumen flow rate up to the calculated rate (See Equation 2 below). At the same time bring the average trans membrane pressure (TMP) up to 5 psi. (See Equation 5 below).

Next, the fibers are deglycerinized by flushing flush 500 ml of fresh water (Milli-Q) through the devices without recirculating. Water should be dripping through the membrane. If you can not see any water flowing, refill inlet reservoir, and allow another 10–15 minutes to pass before continuing. Once the fibers are wet they must stay wet and not allowed to dry out. The inlet and outlet pressure must not be greater than 10%. If it is, a new cartridge must be made.

Next, hydraulic permeability is calculated from Equation 5 and expressed in ml/min/m²/mm Hg (see Equation 4 for effective surface area, and Equation 6 for psi to mm Hg conversion). The ultra filtrate flow through the wills of the fibers is measured by placing the filtrate port in a graduated cylinder and collecting for 10 minutes. Record the volume collected, inlet and outlet pressures, number of fibers in the cartridge, and length of fibers between epoxy ends for the timed measurement.

Equations Used

1. Shear Rate:

$$Q_L = (nd^3 \gamma_w)/1.64 \times 10^{11}$$

where:
$\gamma_w$ = 2,000 sec$^{-1}$
d = inner diameter of the fiber in microns
$Q_L$ = average flow through the fiber lumens in ml/min.
n = number of fibers in the device 2. Average Trans Membrane Pressure (TMP):

$$TMP = (P_i + P_o)/2$$

where:
P$_i$=inlet pressure
P$_o$=outlet pressure

3. Effective Surface Area:

$$m2 = \pi n d l$$

n=number of fibers in the device
d=inner diameter of the fiber in meters
l=effective length of fibers from potting compound interfaces in meters 4. Hydraulic Permeability:
Hydro. Perm.=ml/min./m$^2$/mm Hg 5. Conversion: psi to mm Hg:
mm Hg=psi×51.7

Molecular Weight Cut-Off Characterization:

The fibers are also characterized for convective Molecular Weight Cut-Off (MWCO). To do so, a Gel Permeation Chromatography (GPC) calibration curve must first be produced.

Using a 1 cc syringe and 0.221μ cellulose acetate filter (Corning #21052-25), filter 0.5 ml of dextran filtrate sample (Dextran) into a GPC screw top vial then cap. Repeat step one for reservoir dextran sample. Repeat for all samples. Samples are now ready for injection. Refer to GPC Calibration SOP # for GPC parameters and run conditions.

The relative dextran concentration as a function of Mw is determined by integrating the GPC chromatograns into 40 slices over a retention time bracketing the standards. The upper integration time limit is determined from the retention time of the 5,800 standard and the lower integration time limit is determined from the retention time of the 853,000 standard. The dextran Mw for each slice is calculated from the retention time of the midpoint of the slice using the calibration curve. The rejection coefficient as a function of dextran Mw is calculated according to the equation 1.

The Molecular weight cut-off of the hollow fiber membrane is determined as the molecular weight at the 90% rejection coefficient. If the calculated rejections from the 40 GPC slices do not report a molecular weight at a 90% rejection, a linear interpolation is used to calculate a molecular weight at 90% rejection.

Equations:
1. Rejection Coefficient $$\%R(Mw) = 100 - [100 \times (C_F(Mw)/C_R(Mw))]$$

Where
%R(Mw)=rejection coefficient at dextran molecular weight Mw
$C_F$=Filtrate OPC slice area at dextran molecular weight Mw
$C_R$=a Reservoir GPC slice area at dextran molecular weight Mw Example 3

Production of BHK cells producing CNTF cell line

The human CNTF (hCNTF) gene was inserted into a dihydrofolate reductase (DHFR) based expression vector designated PNUT, which contains the entire pUC 18 sequence including the polylinker. See Baetge et al., *Proc. Natl. Acad. Sci. USA*, 83, pp. 5454–58 (1986). The DNA and amino acid sequence of CNTF is known. See U.S. Pat. No. 4,997,929, incorporated herein by reference.

The transcription of the cDNA encoding the mutant form of DHFR is driven by the SV40 promoter. The 3' end is fused with the 3' end of the hepatitis B virus gene (HBV 3') to ensure efficient polyadenylation and maturation signals.

The hCNTF gene was obtained by PCR amplification of human DNA. The primers used contained EcoRI site at the position of the natural hCNTF initiation codon. The hCNTF gene was fused at its 5' extremity to 150 bp sequence coming from the mouse immunoglobulin (Ig) gene. The EcoRI site was used in such a way that the amino terminal part of the hCNTF protein corresponds to the first 18 amino acids of the Ig gene. A 325 bp hGH AvaI fragment containing the polyadenylation sequence and other sequences important for maturation of the mRNA was cloned at the 3' extremity of the hCNTF gene. Briefly, this fragment we introduced in the SpeI site of the Bluescript polylinker creating a BamHI and NotI site at the 5' and 3' end, respectively. Then the BamHI site was litigated to the BglII site engineered at the 3' end hCNTF.

This construction was inserted at the position +6 of the mouse MT-I promoter and the entire 3050 bp MT/Ig/hCNTF/hGH KpnI-NotI fragment was inserted in the KpnI-NotI site of the pNUT vector. Finally, the HSV-TK gene was cloned in the NotI site of the vector, thus separating it from the DHFR gene by the entire pUC-18 plasmid. This final construction is named RP3224E2.

The RP3224E2 vector DNA was amplified in a standard *E.coli* strain (BH101) and purified by the Qiagen-Plasmid Kit (Kontron). DNA was transfected using a standard calcium/phosphate transfection procedure and selected with increasing concentrations of methotrexate. Cells are selected continuously in methotrexate while maintained in PC-1 tissue culture medium. The PC-1 medium is a defined medium containing protein from human recombinant sources.

Following drug selection (25 to 200 μm methrotrexate), the BHK cells were maintained in vitro without drug selection for several months and showed no loss of growth factor expression as assessed by Northern blot analysis, bioassays or ELISA. The level of CNTF production was around 1.0 ng/10$^3$ cells/hour as determined by bioassay and by ELISA.

Example 4

BHK-hCNTF cells encapsulated in PES μp fibers, implanted into rodents

BAO Fabrication

BAOs were fabricated from the PES μp membranes of Example 1 as follows: Pre-assembled devices (PADs) were manufactured by affixing a length of 6±0.5 mm dry hollow fiber onto a light cured septal-hub assembly (the trailing end) with a light-cured acrylate (Luxtrak™ LCM 23, ICI Resins US, Wilmington, Mass.). The septal-hub had loading access for cells to be injected into the lumen of the device. The remaining end (leading end) is likewise sealed with the LCM 23. PADs were sterilized by either ethylene oxide exposure or immersion in 70% filter sterilized ethanol for 45 minutes. Sterilized PADs were placed in Hanks' balanced salts (HBSS) prior to the encapsulation procedure.

Encapsulation

BHK cells were encapsulated in BAOs as described herein. BHK cells were grown in DMEM, 10% fetal bovine serum, antibiotic/antimycotic, and L-glutamine (Gibco) in 5% CO$_2$ and at 37° C. BHK cells (transfected according to Example 3 or untransfected) were selected in medium containing 200 μM methotrexate (Sigma) for 3–4 weeks. Resistant cells were maintained as a polyclonal population either with or without 200 μM methotrexate. Thereafter, clones were selected and characterized for expression and release of their transgene. Unless otherwise indicated, mock-transfected cells served as controls in these examples. The cells were removed from the culture plates with trypsin/EDTA and prepared as a single-cell suspension. The BHK cell suspensions at a density of $2\times10^7$ cells/ml were mixed 1:1 with the physiologic bovine dermal collagen Vitrogen® 3–3.5 mg/ml (Celtrix, Palo Alto, Calif.), and infused into the PADs through the septal access port. Two clonal ines were used for further study, clones 39 and 72.

After infusing $2\pm0.3$ $\mu l$ of the cellular suspension, the septum was cracked off and the access port was sealed using the LCM 23 light-cured acrylate. BHK cell-loaded devices were maintained in PC-1 medium 3–5 days prior to implantation. After 3 or 4 days, the capsules were rinsed in HBSS, placed in a multiwell containing 1 ml of fresh PC-1 medium overnight to be analyzed for hNGF or hCNTF by ELISA.

Implantation into Rodents

The BAOs with $\mu p$ hydrophilic PES hollow fiber membranes were bilaterally implanted stereotaxically into rat striatum for 30 days and supraspinally implanted subcutaneously in neonatal mice and rats for 90 days. Device performance was characterized based on BHK cell survival (viability) and host tissue reaction to the final encapsulated devices.

Results

BHK cell containing devices were held in vitro for at least 8 weeks, and were found to contain abundant, healthy cells. After 4 weeks in vivo, the implants were removed and examined histologically. Of the striatal implants, five out of five devices showed the presence of viable cells at 4 weeks. However, one of the devices had a failed seal and a resulting immunologic reaction. In the striatal implants, we also had 5 empty devices to look at the host tissue reaction. The devices showed excellent biocompatibility.

Example 5

BHK engineered cells to produce CNTF implanted into sheep w/PES #5 membrane

Cell Suspension Concentration for Encapsulation

BHK engineered cells made according to Example 3 were encapsulated at a concentration of $1\times10^4$ cells/$\mu l$ in 3.5 mg/ml of Zyderm (Collagen Corp.). Zyderm was diluted using PBS Dulbecco's media. Capsules were stored in PC-1 medial.

The capsules were fabricated using PES #5 membrane made by Example 1 above (500$\mu$ ID, 100$\mu$ wall) in hub sealed devices and the BAO fabrication and encapsulation procedure of Example 4.

Implantation Into Sheep

Next, the capsules were implanted into sheep. Sheep weighing 42–90 kg (69±15) were given general, endotracheal anesthesia (pentobarbital sodium 10 mg/kg iv; halothane 0.5–2%) and preoperative antibiotics (cefaxolin sodium 1 g iv). The animals were positioned in the prone position and the operating table tilted head up to 30°. A 5l0 cm parasaggital lumbar incision was made and a spinal tap performed with a Tuohy needle between L4 and L5 via an oblique paramedian approach. The appropriate position of the needle in the subarachnoid space was confirmed by withdrawal of several mls of CSF. This CSF was analyzed for cell counts, protein level, and microbiology. A guide wire was introduced through the lumen of the Ruohy needle until it extended 4–5 cm cranially from the needle opening. The Tuohy needle was removed and a 7 French dilator introduced over the guide wire to the level of the dura and removed, enlarging the wire track through the fascia, paraspinous muscle and ligamentum flavum. This allowed a 6 French dilator with a 20 cm long outer cannula sheath to be advanced into the subarachnoid space until the tip of the cannula was positioned 7 cm within the space. The guide wire and the dilator were then removed, leaving the cannula within the subarachnoid space to act as a protective guide for insertion of the encapsule.

The cell-loaded and fully assembled device was delivered into the operating room in a sterile container, bathed in PC-1 medium. The device was prepared for insertion by mounting the tether on a stainless steel pusher which served to stiffen the very flexible tether and allowed the capsule to be manipulated within the lumen of the cannula. The membrane portion of the device was then introduced into the cannula, handling the device by the silicone tether and the handle of the pusher. The device was advanced until the membrane portion lay entirely within the CSF containing subarachnoid space. The cannula was then removed while the device was maintained in position using the pusher. Finally, the pusher was removed and the silicone tether anchored at its free end by a nonabsorbable suture and completely covered with a 2 layer closure of skin and subcutaneous tissue.

The animal was recovered, examined for possible neurological complications, and returned to the farm for boarding on the day of implantation. All animals were able to return to normal diet and activity on the day of surgery. All experimental, animal care and surgical protocols were approved by the Canton of Vaud Committee on animal research.

A total of six female sheep were implanted in the intrathecal space. Two animals were sacrificed at 30 days and 4 animals at 90 days.

All animals were monitored for infection, inflammation or any distress. Possible side effects of CNTF are fever, weight loss, nausea and reactivation to herpes. The temperatures and weight of the animals was monitored throughout the experiment.

Results

Figure 5:
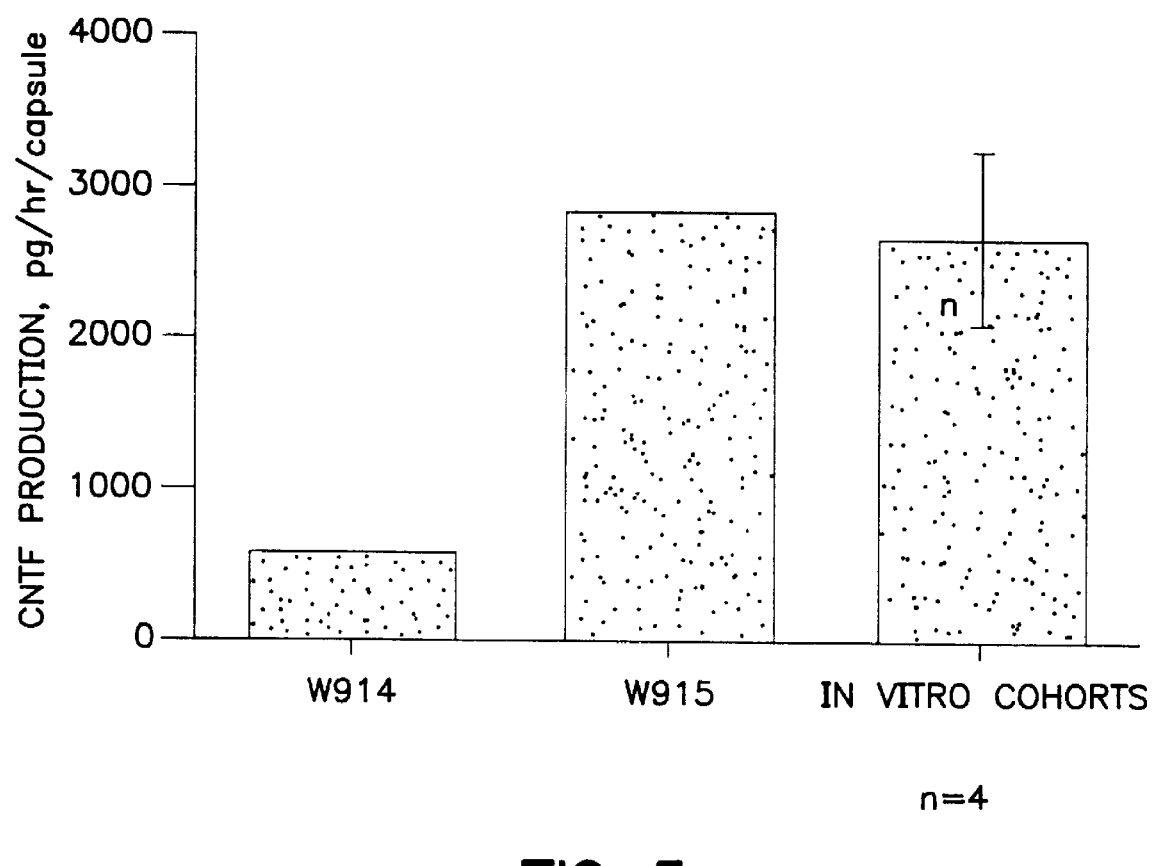
FIG. 5 is a graph showing CNTF output of BAOs containing BHK cells encapsulated in PES #5 membranes following a 1 month implantation period in sheep.

CNTF levels were measured from the explanted capsules—see FIG. 5. The explants shows the presence of viable cells.

Example 6

BHK-GDNF cells encapsulated in PES $\mu p$ membranes implanted in rodents

BAOs were fabricated from the PES $\mu p$ membrane of Example 1. BAO devices were prepared as in Example 4 above. BHK cells were genetically engineered to secrete Glial Derived Neurotrophic Factor (GDNF) substantially as described in Example 1, using the known sequence encoding GDNF. Lin, WO 93/06116.

Figure 4:
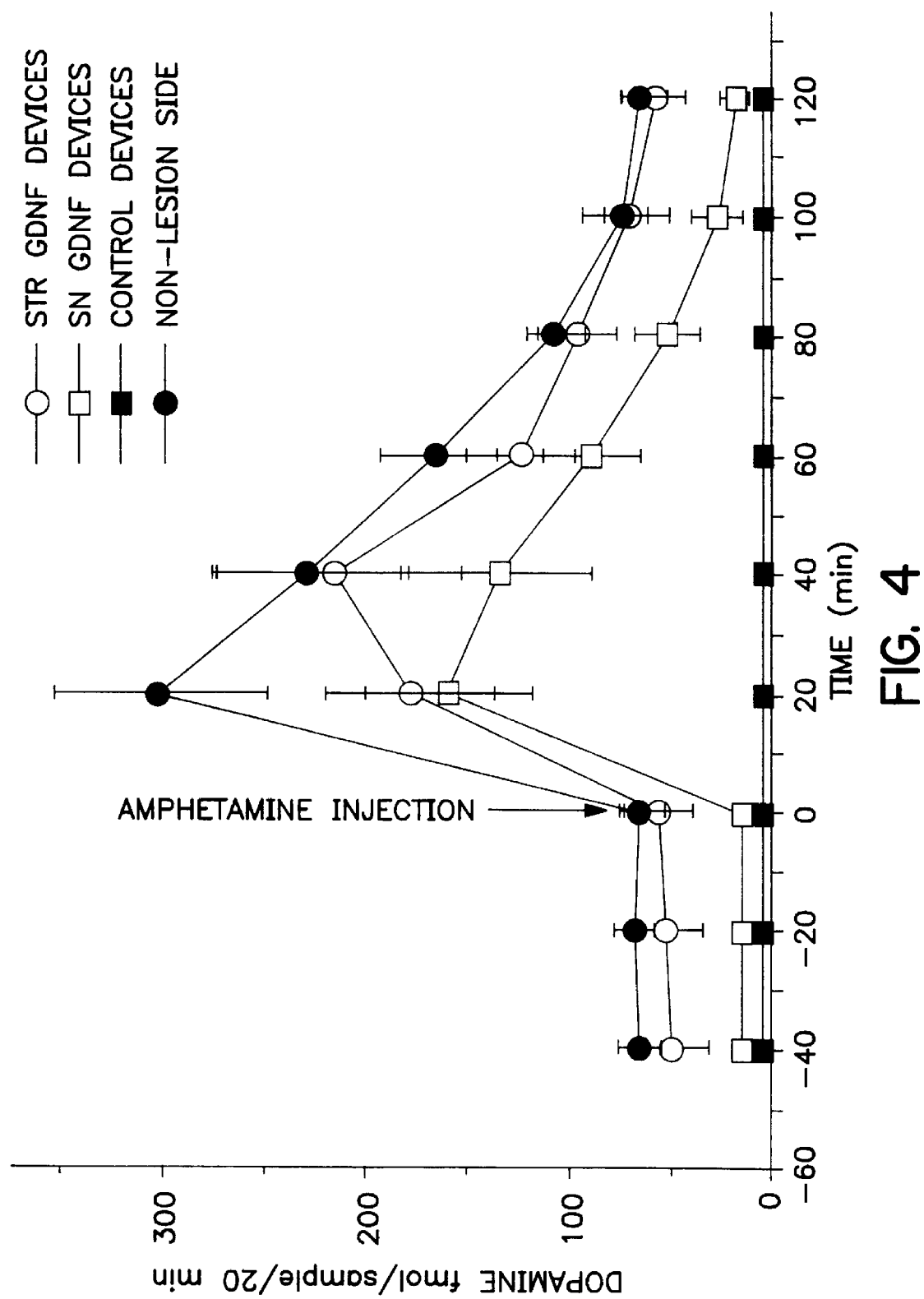
FIG. 4 is a graph showing microdialysis of GDNF Secreting BAOs of this invention.

Rats received unilateral lesions of the substantia nigra with 6-OHDA. Thirty days later, BHK containing devices were implanted in either the striatum or the substantia nigra. Untransfected BHK cell containing devices served as the control. Guide cannulae were implanted bilaterally in the striatum. Thirty to forty days later, dialysis was performed to determine basal and amphetamine stimulated levels of dopamine. Rats were subsequently sacrificed and either tissue levels of dopamine determined or histology performed. See FIG. 4.

Subjects that received GDNF producing devices had higher basal and nicotine stimulated levels of extracellular dopamine than control subjects. The GDNF subjects also had higher tissue levels of dopamine than did control subjects. Histology revealed greater tyrosine hydroxylase (TH) staining in GDNF subjects compared to controls. This was greatest adjacent to the device. Histology revealed no adverse reaction to either GDNF secreting capsules or control capsules.

Example 7
BHK cells encapsulated in PES μp membranes, implanted into sheep

BOA's were fabricated from the PES μp membrane of Example 1 and BHK cells. The BAOs were implanted into the subarachnoid space of sheep for 30 days according to the procedure of Example 5. After 30 days, the capsules showed abundant live cells.

Example 8
BHK cells encapsulated in PAN/PVC type 4 fibers, implanted into sheep Prior art BAOs were fabricated from PAN/PVC type 4 double skinned membranes containing BHK cells as follows:

Hollow fibers were spun from a 12.5–13.5% poly (acrylonitrile vinylchloride) solution by a wet spinning technique. Cabasso, *Hollow Fiber Membranes*, vol. 12, *Kirk-Othmer Encyclopedia of Chemical Technology*, Wiley, N.Y., 3rd Ed. pp. 492–517 (1980). The resulting hollow fiber had an outside diameter (OD) of around 900 μm and a wall thickness of around 150 μm. The fibers had a hydraulic permeability of 18 ml/min/m$^2$/mmHg and a rejection coefficient of more than 90% for bovine serum albumin. Fibers were impregnated with glycerine for storage purposes.

In order to make implantable capsules, lengths of fiber were first cut into 5 cm long segments and the distal extremity of each segment was sealed with an acrylic glue. Encapsulation hub assemblies were prepared by providing lengths of the membrane described above, sealing one end of the fiber with a single drop of LCM 24 (Light curable acrylate glue, available from ICI), and curing the glue with blue light, and repeating the step with a second drop. The opposite end was previously attached to a frangible necked hub assembly, having a silicone septum through which the cell solution may be introduced. The fiber was glued to the hub assembly by applying LCM 22 to the outer diameter of the hub assembly, and pulling the fiber up over it, and curing with blue light. The hub/fiber assemblies were placed in sterilization bags and were ETO sterilized.

Following sterilization with ethylene oxide and outgassing, the fibers were deglycerinated by ultrafiltering first 70% EtOH, and then HEPES buffered saline solution through the walls of the fiber under vacuum.

A 2% alginate solution was prepared dissolving 1 g of Protan Ultrapure alginate which had been cold cycle ETO sterilized in 50 mL of HEPES buffered 0.9% NaCl. A cell solution was created by diluting in the ratio of two parts alginate solution to one part BHK cell solution.

The cell/alginate suspension (approx. 20×10$^6$ cells/100 μl) was placed in a 1 ml syringe. A Hamilton 1800 Series 50 microliter syringe was set for a 15 microliter air bubble, and was inserted into a 1 ml syringe containing the cell solution and 30 microliters were drawn up. The cell solution was injected through the silicone seal of the hub/fiber assembly into the lumen of a modacrylic hollow fiber membrane with a molecular weight cutoff of approximately 50,000 daltons. Ultrafiltration could be observed along the entire length of the fiber. After one minute, the hub was snapped off the sub-hub, exposing a fresh surface, unwet by cell solution. A single drop of LCM 24 was applied and the adhesive was cured with blue light. The device was placed first in HEPES buffered NaCl solution and then in CaCl$_2$ solution for five minutes to cross-link the alginate. Each implant was about 5 cm long, 1 mm in diameter, and contained approximately 2.5 million cells.

After the devices were filled and sealed a silicone tether (Speciality Silcone Fabrication, Paso Robles, Calif.) (ID: 0.69, OD: 1.25) was then placed over the proximal end of the fiber. A radiopaque titanium plug was inserted in the lumen of the silicone tether to act as a radiographic marker. The devices were then placed in 100 mm tissue culture dishes in 1.5 ml PC-1 medium, and stored at 37° C., in a 5% CO$_2$ incubator for in vitro analysis and for storage until implantation.

The encapsulated cells were then implanted into the subarachnoid space of sheep for 30 days according to the procedure of Example 5.

After 30 days, unlike the capsules from the explanted capsules of Example 7, the capsules showed no live cells.

Example 9
BHK cells engineered to secrete CNTF encapsulated in PES #5 capsules at 50×10$^3$ cells/μl, implanted into rodents 5 rats received 20 mm long BAOs fabricated from the PES#5 membranes of Example 1 loaded with clone 39 cells of Example 4. The cell loading density was 50×10$^3$ cells μl. The volume of the BAO was 4 μl. The CNTF released by each capsule was measured on day 1 by the R&D CNTF Elisa system. At day 2, the BAOs were placed in the subarachnoid space over the spinal cord through a laminectomy performed at the L1–L2 level. The animals were then closely observed for 7 days during which their rectal temperature, their weight and their behavior was monitored.

Cerebrospinal fluid (CSF) was collected at the time of sacrifice for CNTF determination through an occipital tap. The retrieved capsules were fixed in 4% paraformaldehyde solution. The animals were transcardially perfused with a 4% paraformaldehyde solution. The spinal cord was then inspected and dissected out. Biocompatibility and viability of the encapsulated cells was assessed on glycolmethacrylate sections. Potential toxicity of CNTF on nervous tissue was assessed on frozen sections of the spinal cord using the following staining methods. General morphology was analyzed on Nissl stain, astrocytic reaction on GFAP immunohistochemistry, microglia reactivity using loctine bandeira simplicifolia immunhistochemistry.

Figure 6:
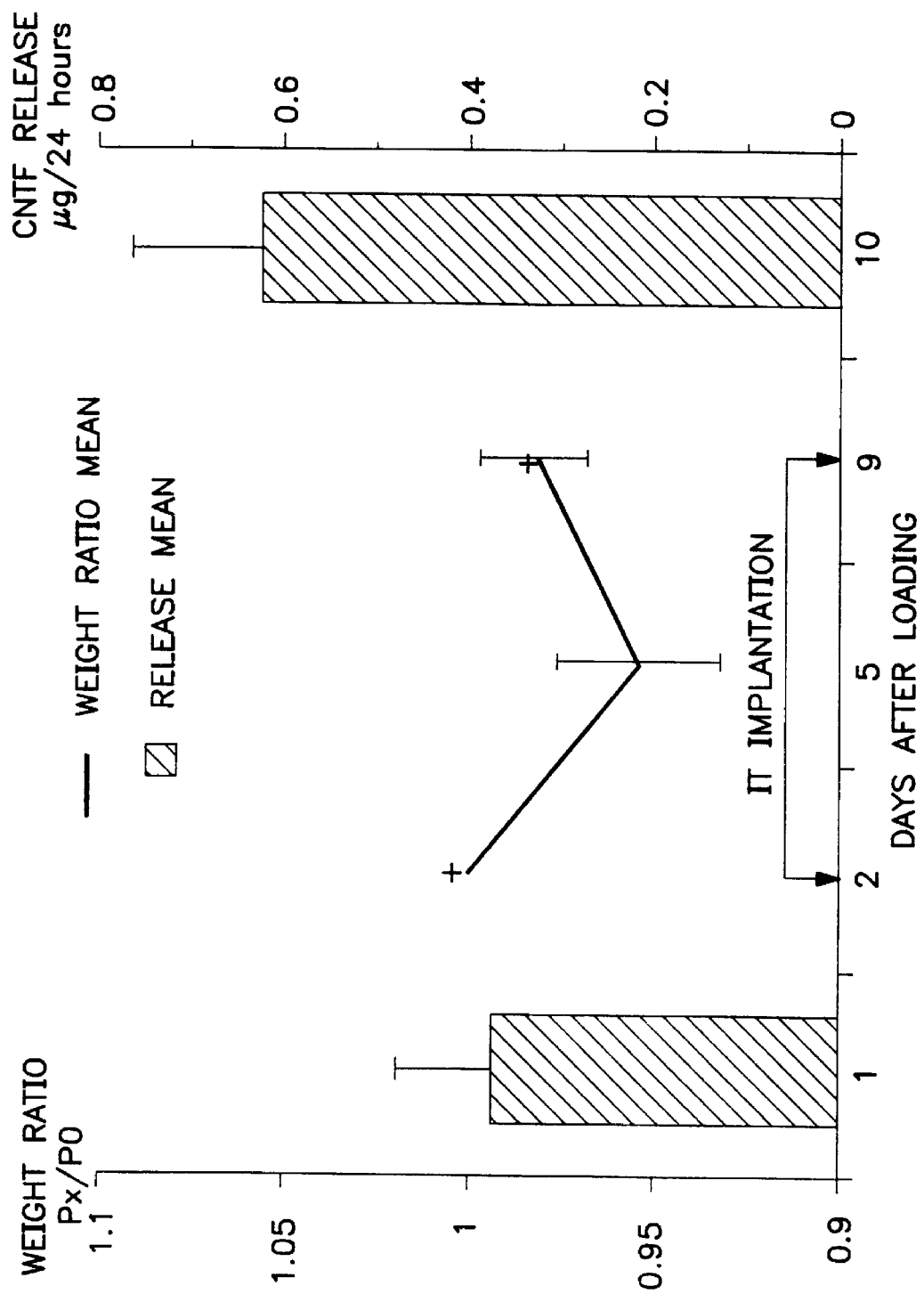
FIG. 6 is a graph of the rat body weight ratio from day 0 to day 10 after implantation of a BAO containing BHK cells secreting CNTF loaded at a density of $50 \times 10^3$ cells/$\mu$l into a PES #5 capsule. The graph also shows the amount of CNTF secreted.
Figure 7:
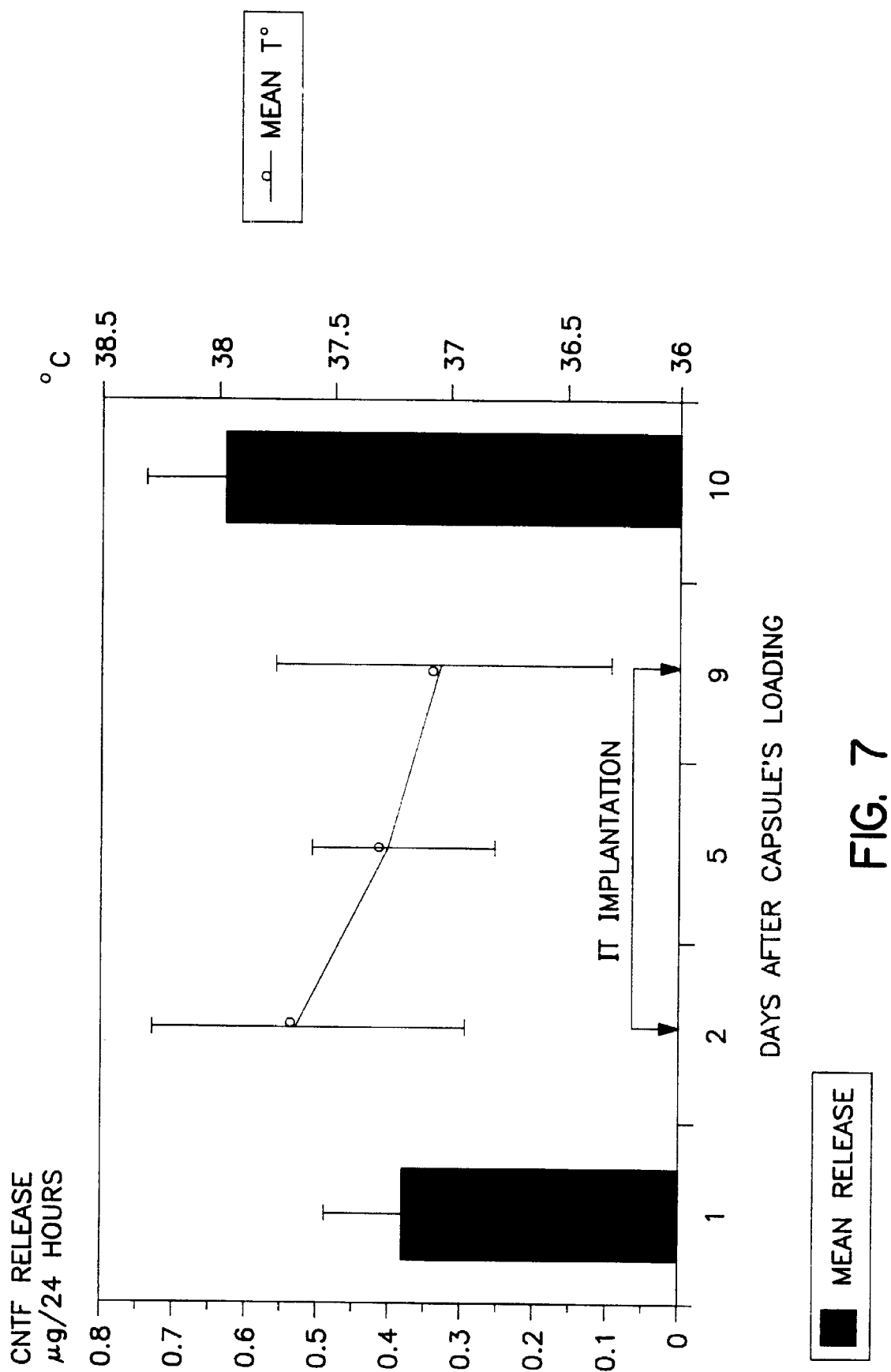
FIG. 7 is a graph of rat body temperature from day 1 to day 10 following implant of a BAO containing BHK cells secreting CNTF loaded at a density of $50 \times 10^3$ cells/$\mu$l in a PES #5 capsule. The graph also shows the amount of CNTF secreted.

No adverse effect was observed on the general behavior of the implanted animals. No significant variation of the animal's weight or temperature was seen (FIG. 6 and 7).

By comparison, the intraventricular delivery of 2.4 to 60 μg of BDNF per day induces a 10 to 20% weight loss over one week. Q. Yan et al., 14, *J. Neurosci*, pp. 5281–5291, 1994. More CNTF was released at the time of explant as compared to preimplant values (0.368 +/− 0.108 versus 0.623 +/− 0.145 μg respectively). In 2 rats, the measured CSF CNTF levels were 78 and 712 pg/ml respectively. However these values might be underestimated as the needles used to collect the CSF samples were not albuminated.

The retrieved capsules were devoid of any macroscopic tissue adhesion. The microscopic evaluation of the capsules revealed excellent biocompatibility with only a few isolated cells adhering to the capsules. Histological examination of the spinal cord showed no gross reactivity. The meninglia appeared normal. Neuronal populations especially the ventral horn motoneuron population were of normal appearance. Only minimal GFAP and lectine bandeira simplicifolia reactivity was observed.

Example 10
BHK cells engineered to secrete CNTF encapsulated in PES #5 and #7 capsules at 10×10$^3$ cells/μl, implanted into rodents A total of nineteen rats were implanted with BAOs containing CNTF-secreting BHK cells. Ten animals received a 2 mm BAO comprising a PES#5 capsule loaded with either clone 39 (n=5) or clone 72 cells (n=5). The remaining 9 animals received a 2 mm long BAO comprising a PES#7 membrane capsule loaded with either clone 39 (n=5) or clone 72 cells (n=4). The cell loading density was $10 \times 10^3$ cells/µAl. The BAOs were kept 3 days in vitro before implantation. The CNTF released by each BAO was measured at day 1 post-loading. No abnormalities in behavior, body temperature or weight was observed during the first 2 weeks.

Half of the animals were sacrificed at 2 weeks, the other half will be kept alive for 3 months. Histological analysis of the first half is in process.

This experiment corrected a prior experiment, in which the BHK cells were loaded at a density of $50 \times 10^3$ cells/µl and were tested for CNTF release at day 4 and implanted at day 6, and which resulted in a fairly important central necrosis in the core of the capsules.

Example 11

PC12 cells encapsulated in PES µp membranes, implanted into monkeys

BAOs were fabricated from the PES µp membrane of Example 1. PC12 cells were encapsulated according to Example 4. The BAOs were then implanted into primate parenchyma for 16 weeks according to the following procedure:

We used cynomologous monkeys, housed one per cage for the duration of the study on a 12 hr on/12 hr off lighting schedule with food and water available ad libitum. The level of care for these animals exceeded that recommended by the National Institutes of Health.

Briefly, we first transquilized the monkeys with ketamine (10 mg/kg, im) and then induced anesthesia with isoflurane (1–2%).

We then placed the monkeys in a Kopf stereotaxic apparatus. Under sterile conditions, we made a U-shaped incision based on the midline exposing the skull overlying the right striatum. We then made a 2 cm×3 cm carniotomy overlying the striatum using a high speed drill and the dura was reflected in a U-shaped manner. We stereotaxically placed polymer capsule implants into the head of the caudate nucleus and three capsules into the putamen. We cut the tether at the surface of the cortex to facilitate later identification and retrieval. We then reapproximated and sutured the dura and the skull cap back into place, sutured subcutaneous tissues with 4-0 Coated Vicryl inverted sutures and closed the skin with 4-0 Ethilon sutures in a routine fashion.

After 16 weeks the capsules were retrieved and were found to have few or no viable cells.

Example 12

PC12 Cells encapsulated in PES #5,7,9 membranes, implanted into monkeys

BAOs were fabricated from the PES #5, 7, 9 membranes of Example 1. PC12 cells were encapsulated and implanted into primate parenchyma for 16 weeks according to the procedure in Example 11. No or very few viable cells were found.

Example 13

BHK-hCNTF cells encapsulated in PES #5 human-type capsules (in vitro)

BAOs were fabricated substantially as described in Examples 3, 4 and 5, containing CNTF-secreting BHK cells in PES #5 membrane capsules.

In order to evaluate the stability of CNTF release from these BAOS, 5 cm long capsules made from PES #5 membrane of example 1 were loaded with either clone 39 (n=3) or clone 72 (n=3) cells. The cell loading density was $10 \times 10^3$ cells/µl. The total volume of each capsule was 10 µl. The capsules were kept in PC1 medium for 2 months in vitro. The capsules were then fixed in a 4% formaldehyde solution, embedded in glycolmethacrylate, cut and stained with methylene blue.

The CNTF released from each capsule was measured 5, 11, 14, 28 and 56 days post-loading by immersing each capsule in 2 ml of fresh PC1 medium for 30 min. CNTF determination was then performed on the collected medium using the R&D Elisa system.

Figure 8:
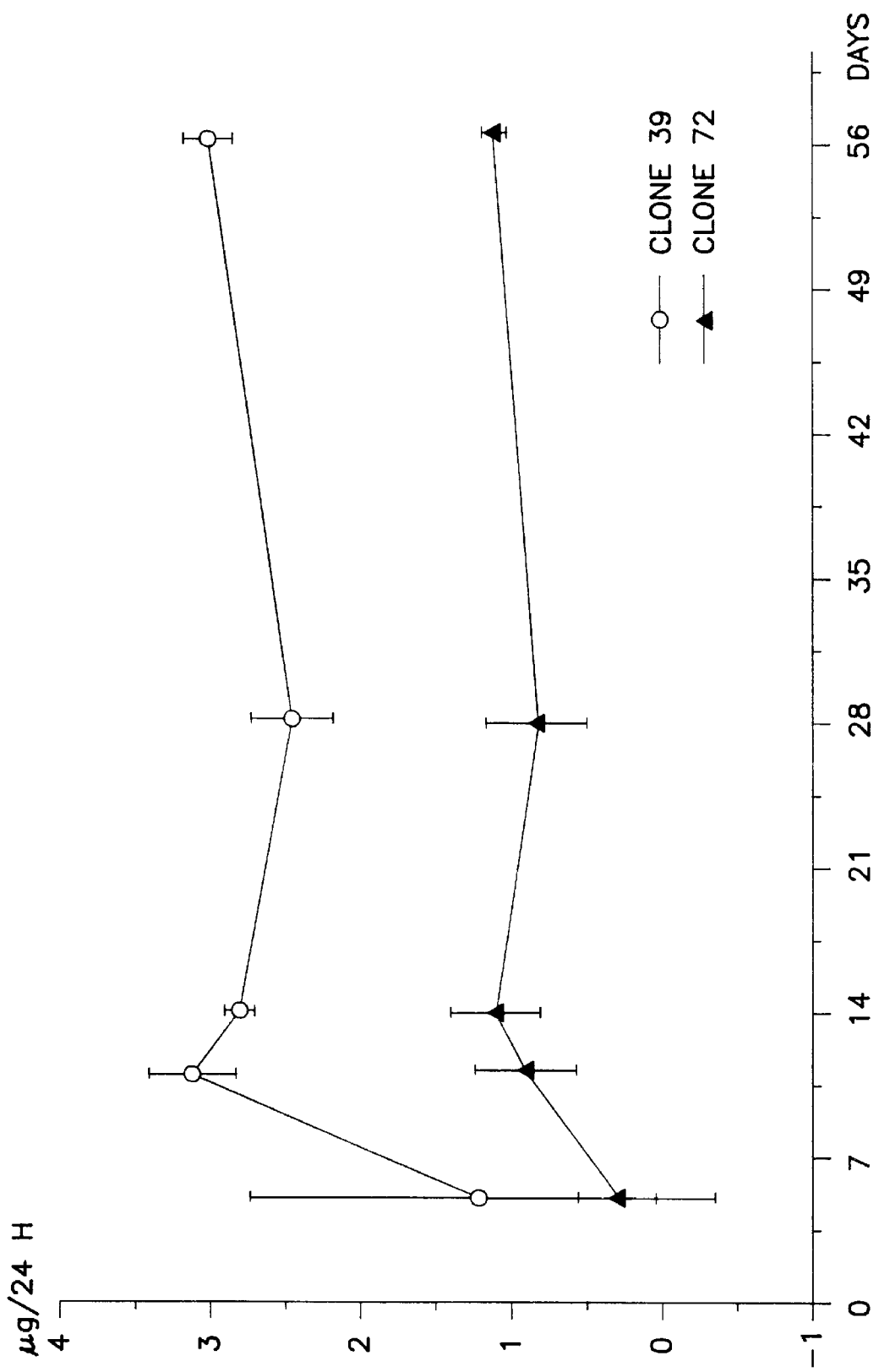
FIGS. 8 and 9 are graphs of CNTF release in vitro by a BAO containing BHK cells in a PES #5 capsule over a period of 56 days.
Figure 9:
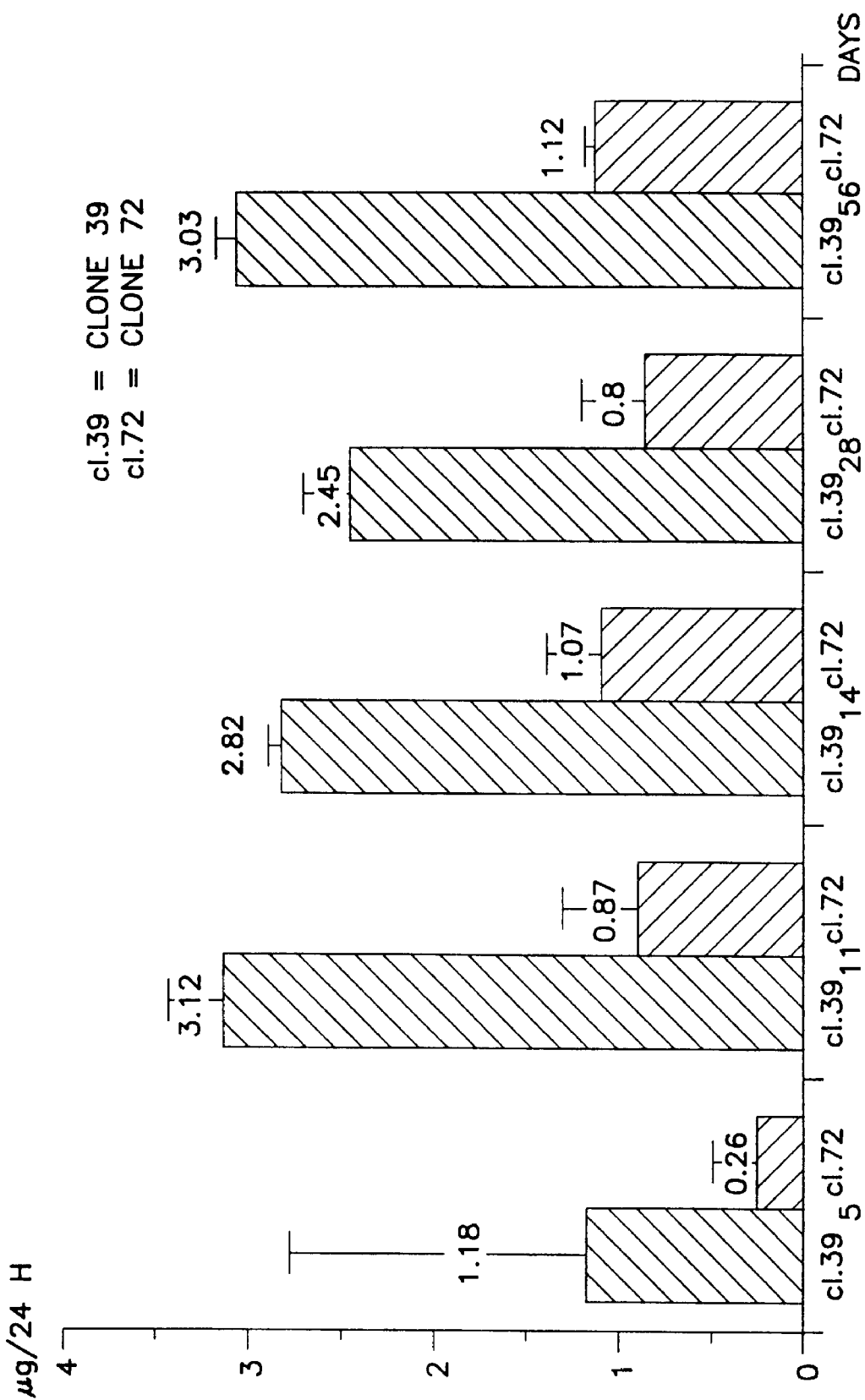

The results show an increase of CNTF release up to 2 weeks followed by a stable release up to 2 months (FIG. 8 and 9). Capsules loaded with clone 39 released in the order of 3 µg per day whereas those loaded with clone 72 released in the order of 1 µg per day. Histological examination showed large numbers of BHK cells surrounding small necrotic cores.

Example 14

BHK-hCNTF cells encapsulated in PES#5 fibers, implanted in the human subarachnoid space for the treatment of amyotrophic lateral sclerosis.

BAOs were fabricated as described in Examples 3,4 and 5, containing CNTF-secreting BHK cells in PES #5 membrane capsules.

Subjects were patients diagnosed with ALS as manifested by a combination of both upper motor neuron and lower motor neuron deficits at multiple levels; confirmatory electrophysisiologic studies demonstrating active and chronic denervation in 3 limbs or 2 limbs and bulbar musculature; no neurological involvement outside the voluntary motor system; no evidence of primary disease that could cause neurologic deficit, particularly cervical spondylosis of plasma cell dyscrasia. The patient is relatively strong, i.e. can walk by himself and is early in the course of the disease. The patient has forced vital capacity >75% of normal at the time of entry.

Devices was loaded at a density of $2 \times 10^5$ transfected cells/µl of collagen solution (Zyderm). The devices were fabricated from PES #5 fiber and were 5 cm long. The capsules delivered a dosage of CNTF of 1µ/day intrathecally. Each patient received one device.

Implantation procedure was as follows:

Surgical Procedure

After establishing IV access and administering prophylactic antibiotics (cefazolin sodium, 1 gram IV), the patient was positioned on the operating table, generally in either the lateral decubitus or genu-pectoral position, with the lumbar spine flexed anteriorly. The operative field was sterily prepared and draped exposing the midline dorsal lumbar region from the levels of S-1 to L-1, and allowing for intraoperative imaging of the lumbar spine with C-arm fluoroscopy. Local infiltration with 1.0% lidocaine was used to establish anesthesia of the skin as well as the periosteum and other deep connective tissue structures down to and including the ligamentum flavum.

A 3–5 cm skin incision was made in the parasagital plane 1–2 cm to the right or left of the midline and was continued down to the lumbodorsal fascia using electrocautery for hemostasis. Using traditional bony landmarks including the iliac crests and the lumbar spinous processes, as well as fluoroscopic guidance, and 18 gauge Touhy needle was introduced into the subarachnoid space between L-3 and L-4 via an oblique paramedian approach. The needle was directed so that it entered the space at a shallow, superiorly directed angle that was no greater than 30°–35° with respect to the spinal cord in either the sagittal or transverse plane.

Appropriate position of the tip of the needle was confirmed by withdrawal of several ml of cerebrospinal fluid (CSF) for preimplantation catecholamine, enkephalin, glucose, and protein levels and cell counts.

The Touhy needle hub was reexamined to confirm that the opening at the tip is oriented superiorly (opening direction is marked by the indexing notch for the obturator on the needle hub), and the guide wire was passed down the lumen of the needle until it extended 4–5 cm into the subarachnoid space (determined by premeasuring). Care was taken during passage of the wire that there was not resistance to advancement of the wire out of the needle and that the patient did not complain of significant neurogenic symptoms, either of which observations might indicate misdirection of the guide wire and possible impending nerve root or spinal cord injury.

After the guide wire appeared to be appropriately placed in the subarachnoid space, the Touhy needle was separately withdrawn and removed from the wire. The position of the wire in the midline of the spinal canal, anterior to the expected location of the caud equina, and without kinks or unexplainable bends was then confirmed with fluoroscopy. After removal of the Touhy needle the guide wire should be able to be moved freely into and out of the space with only very slight resistance due to the rough surface of the wire running through the dense and fibrous ligamentum flavum.

The 7 French dilator was then placed over the guide wire and the wire was used to direct the dilator as it was gently but firmly pushed through the fascia, paraspinous muscle, and ligamentum flavum, following the track of the wire toward the subarachnoid space. Advancement of the 7 French dilator was stopped and the dilator removed from the wire as soon as a loss of resistance was detected after passing the ligamentum flavum. This was done in order to avoid advancing and manipulating this relatively rigid dilator within the subarachnoid space to any significant degree.

After the wire track was "overdilated" by the 7 French dilator, the 6 French dilator and cannula sheath were assembled and placed over the guide wire. The 6 French dilator and cannula were advanced carefully into the subarachnoid space until the opening tip of the cannula was positioned 7 cm within the space. As with the 7 French dilator, the assembled 6 French dilator and cannula were directed by the wire within the lumen of the dilator. Position within the subarachnoid space was determined by premeasuring the device and was grossly confirmed by fluoroscopy. Great care was taken with manipulation of the dilators and cannula within the subarachnoid space to avoid misdirection and possible neurologic injury.

When appropriate positioning of the cannula was assured, the guide wire and the 6 French dilator were gently removed from the lumen of the cannula in sequence. Depending on the patient's position on the operating table, CSF flow through the cannula at this point should be noticeable and may be very brisk, requiring capping the cannula or very prompt placement of the BAO implant in order to prevent excessive CSF.

The BAO was provided in a sterile, double envelope container, bathed in transport medium, and fully assembled including a tubular silicone tether. Prior to implantation through the cannula and into the subarachnoid space, the BAO was transferred to the insertion kit tray where it was positioned in a location that allowed the BAO to be maintained in transport medium while it was grossly examined for damage or major defects, and while the silicone tether was trimmed, adjusting its length to the pusher and removing the hemaclip™ that plugs its external end.

The tether portion of the BAO was mounted onto the stainless steel pusher by inserting the small diameter wire portion of the pusher as the membrane portion of the device was carefully introduced into the cannula. The BAO was advanced until the tip of the membrane reached a point that was 2–10 mm within the cranial tip of the cannula in the subarachnoid space. This placement was achieved by premeasuring the cannula and the BAO-tether-pusher assembly, and it assured that the membrane portion of the BAO was protected by the cannula for the entire time that it was being advanced into position.

After the BAO was positioned within the cannula, the pusher was used to hold the BAO in position (without advancing or withdrawing) in the subarachnoid space while the cannula was completely withdrawn from over the BAO and pusher. The pusher was then removed from the BAO by sliding its wire portion out of the silicone tether. Using this method the final placement of the BAO was such that the 5 cm long membrane portion of the BAO lay entirely within the CSF containing subarachnoid space ventral to the cauda equina. It was anchored at its caudal end by a roughly 1–cm length of silicone tether that ran within the subarachnoid space before the tether exited through the dura and ligamentum flavum. The tether continued externally from this level through the paraspinous muscle and emerged from the lumbodorsal fascia leaving generally 10–12 cm of free tether material that was available for securing the device.

CSF leakage was minimized by injecting fibrin glue (Tisse®) into the track occupied by the tether in the paraspinous muscle, and by firmly closing the superficial fascial opening of the track with a purse-string suture. The free end of the tether was then anchored with non-absorbable suture and completely covered with a 2 layer closure of the skin and subcutaneous tissue.

The patient was then transferred to the neurosurgical recovery area and kept at strict bed rest, recumbent, for 24 hours postoperatively. Antibiotic prophylaxis is also continued for 24 hours following the implantation procedure.

The patients were monitored every day during the first week, once a week from the second to the fourth week and once a month thereafter, for, inter alia, side effects such as fever, stomatitis, cough and the reactivation to herpes. The following tests were performed once a month for efficacy evaluation: Tufts Quantitative Neurological Exam (TQNE); Bulbar coordination; Respiratory function—forced vital capacity, inspiratory flow. Blood was drawn once a week for the first four week and once a month thereafter for detection of plasma CNTF, potential antibodies to CNTF, C-reactive protein, fibrinogen.

Two groups of 3 human patients were implanted.

Results

After three months, a spinal tap was performed on the first group of patients. Collected CSF samples were positive for the presence of CNTF. CNTF assay showed readings of between 0.1 and 1 ng/ml CNTF in the three patients tested. Data for the second group of patents is not yet available.

We claim:

1. A bioartificial organ comprising:
   (a) a cell core of one or more living cells, and
   (b) an encapsulating, permselective polyether sulfone membrane shaped to define an internal volume, the cell core of one or more living cells being disposed within the internal volume, the membrane comprising a dense, fine-pored permselective inner region next to the cell core, a middle region that lacks macrovoids, and a fine-pored outer region,
   wherein the fine-pored inner and outer regions of the membrane are interconnected through the middle region via a system of open pores to define an open network structure across the thickness of the membrane, said membrane having a molecular weight cutoff permitting passage of nutrients, but not the passage of cells thereacross to maintain viability of the cell core, and said membrane having pores ranging in size between 0.02 μm and 2.0 μm, the pores have polyhedrally symmetric boundaries and being arranged asymmetrically from one surface of the membrane to the other surface, asymmetry factor AF relative to the maximum pore diameter being 0.01 to 2.0, and ratio of the maximum mean free path length to the diameter of the largest pore being greater than 3.

2. The bioartificial organ of claim 1 wherein the membrane is hydrophilic.

3. The bioartificial organ of claim 1 wherein said cell is a dividing cell.

4. The bioartificial organ of claim 3 wherein said cell produces ciliary neurotrophic factor.

5. The bioartificial organ of claim 3 or 4 wherein said cell is a BHK cell.

6. The bioartificial organ of claim 1 wherein said membrane is microporous.

7. A method of forming a bioartificial organ comprising the step of encapsulating a cell core comprising one or more living cells capable of producing a biologically active product, the step of encapsulating the cell core comprising surrounding the cell core with an encapsulating permselective polyether sulfone membrane, the membrane shaped to define an internal volume, and the membrane comprising a fine-pored permselective inner region next to the cell core, a middle region that lacks macrovoids, and a fine-pored outer region, wherein the fine-pored inner and outer regions of the membrane are interconnected through the middle region via a system of open pores that define an open network structure across the thickness of the membrane, said membrane having a molecular weight cutoff permitting passage of nutrients, but not the passage of cells, thereacross to maintain viability of the cell core, and said membrane having pores ranging in size between 0.02 μm and 2.0 μm, the pores have polyhedrally symmetric boundaries and being arranged asymmetrically from one surface of the membrane to the other surface, asymmetry factor AF relative to the maximum pore diameter being 0.01 to 2.0, and ratio of the maximum mean free path length to the diameter of the largest pore being greater than 3.

8. The method of claim 7 wherein the membrane is formed by coextrusion.

9. The method of claim 7 wherein the membrane is hydrophilic.

10. The method of claim 7 wherein said cell is a dividing cell.

11. The method of claim 10 wherein said cell produces CNTF.

12. The method of claim 10 wherein said cell is a BHK cell.

13. The method of claim 7 wherein said membrane is microporous.

14. A method of providing a biologically active molecule to a recipient, comprising implanting at least one bioartificial organ according to any one of claims 1,2,3 into an implantation site in a recipient, sufficient to provide a therapeutically effective amount of the biologically active molecule.

15. The method of claim 14 wherein the biologically active molecule is selected from the group consisting of ciliary neurotrophic factor, nerve growth factor and glial derived neurotrophic factor.

16. The method of claim 14 wherein the biologically active molecule is ciliary neurotrophic factor.

17. The method of claim 14 wherein the biologically active molecule is selected from the group consisting of endorphins, catecholamines and enkephalins.

18. The method of claim 14 wherein the implantation site is the cerebral spinal fluid.

* * * * *